United States Patent
Lane et al.

(10) Patent No.: US 9,476,889 B2
(45) Date of Patent: Oct. 25, 2016

(54) USE OF ACETYLATED TUBULIN AS A BIOMARKER OF DRUG RESPONSE TO FURAZANOBENZIMIDAZOLES

(75) Inventors: Heidi Alexandra Lane, Therwil (CH); Felix Bachmann, Basel (CH)

(73) Assignee: BASILEA PHARMACEUTICA AG, Basel (CH)

( * ) Notice: Subject to any disclaimer, the term of this patent is extended or adjusted under 35 U.S.C. 154(b) by 0 days.

(21) Appl. No.: 13/983,887

(22) PCT Filed: Feb. 21, 2012

(86) PCT No.: PCT/EP2012/052954
§ 371 (c)(1),
(2), (4) Date: Sep. 16, 2013

(87) PCT Pub. No.: WO2012/113802
PCT Pub. Date: Aug. 30, 2012

(65) Prior Publication Data
US 2014/0005237 A1    Jan. 2, 2014

(30) Foreign Application Priority Data
Feb. 24, 2011   (EP) .................................... 11155774

(51) Int. Cl.
| | | |
|---|---|---|
| A61K 31/415 | (2006.01) | |
| A61K 31/41 | (2006.01) | |
| G01N 33/68 | (2006.01) | |
| A61K 31/4245 | (2006.01) | |
| G01N 33/50 | (2006.01) | |
| A61K 31/4184 | (2006.01) | |
| A61K 31/42 | (2006.01) | |
| A61K 38/00 | (2006.01) | |

(52) U.S. Cl.
CPC ....... *G01N 33/6893* (2013.01); *A61K 31/4245* (2013.01); *G01N 33/5011* (2013.01); *G01N 33/5026* (2013.01); *A61K 31/4184* (2013.01); *A61K 31/42* (2013.01); *A61K 38/00* (2013.01); *G01N 2800/44* (2013.01); *G01N 2800/52* (2013.01)

(58) Field of Classification Search
CPC .. G01N 33/68; A61K 31/42; A61K 31/4184; A61K 31/4245
USPC ................................. 514/394, 395, 361, 364
See application file for complete search history.

(56) References Cited

FOREIGN PATENT DOCUMENTS

| WO | 2004103994 A1 | 12/2004 |
|---|---|---|
| WO | 2006102557 | 9/2006 |

OTHER PUBLICATIONS

Maretta et al., "The presence of acetylated tubulin in the pig thymus," Research in Veterinary Science 79, pp. 89-91, (2005).
Orr et al., "Mechanisms of Taxol resistance related to microtubules," Oncogene 22, pp. 7280-7295, (2003).
Saba et al., Acetylated tubulin (AT) levels predicts response to TPF chemotherapy in locally advanced head and neck squamous cell carcinoma (HNSCC); AACR 101st Annual Meeting Apr. 17-21, Abstract of poster No. 3744, (2010).
Esteve et al., "BAL27862: A unique microtubule-targeted drug that suppresses microtubule dynamics, severs microtubules, and overcomes Cc1-2-and tubulin subtype related drug resistance," AACR 101st Annual Meeting Apr. 17-21, Abstract of poster No. 1977, (2010).
Duran et al., "In vitro activity of the novel tubulin active agent BAL27862 in MDRI (+) and MDRI(-) human breast and ovarian cancer variants selected for resistance to taxanes," AACR 101st Annual Meeting Apr. 17-21, Abstract of poster No. 4412, (2010).

*Primary Examiner* — Kevin E Weddington

(57) ABSTRACT

Use of acetylated tubulin as a biomarker for predicting the response to a compound, preferably resistance of a disease such as cancer in a subject to said compound, wherein the compound is a furazanobenzimidazoles compound of general formula (I).

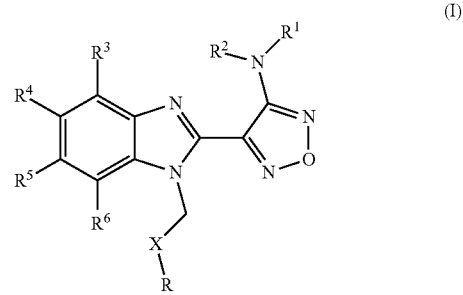

78 Claims, 9 Drawing Sheets

Figure 9

Tubulin alpha-1C chain [Homo sapiens] (SEQ. ID. No. 1)

```
  1 mrecisihvg qagvqignac welyclehgi qpdgqmpsdk tigggddsfn tffsetgagk
 61 hvpravfvdl eptvidevrt gtyrqlfhpe qlitgkedaa nnyarghyti gkeiidlvld
121 rirkladqct glqgflvfhs fgggtgsgft sllmerlsvd ygkksklefs iypapqvsta
181 vvepynsilt thttlehsdc afmvdneaiy dicrrnldie rptytnlnrl isqivssita
241 slrfdgalnv dltefqtnlv pyprihfpla tyapvisaek ayheqltvae itnacfepan
301 qmvkcdprhg kymaccllyr gdvvpkdvna aiatiktkrt iqfvdwcptg fkvginyqpp
361 tvvpggdlak vqravcmlsn ttavaeawar ldhkfdlmya krafvhwyvg egmeegefse
421 aredmaalek dyeevgadsa dgedegeey
```

Figure 10

Tubulin alpha-3C/D chain [Homo sapiens] (SEQ. ID. No. 2)

```
  1 mrecisihvg qagvqignac welyclehgi qpdgqmpsdk tigggddsfn tffsetgagk
 61 hvpravfvdl eptvvdevrt gtyrqlfhpe qlitgkedaa nnyarghyti gkeivdlvld
121 rirkladlct glqgflifhs fgggtgsgfa sllmerlsvd ygkksklefa iypapqvsta
181 vvepynsilt thttlehsdc afmvdneaiy dicrrnldie rptytnlnrl igqivssita
241 slrfdgalnv dltefqtnlv pyprihfpla tyapvisaek ayheqlsvae itnacfepan
301 qmvkcdprhg kymaccmlyr gdvvpkdvna aiatiktkrt iqfvdwcptg fkvginyqpp
361 tvvpggdlak vqravcmlsn ttaiaeawar ldhkfdlmya krafvhwyvg egmeegefse
421 aredlaalek dyeevgvdsv eaeaeegeey
```

Figure 11

Tubulin alpha-4A chain [Homo sapiens] (SEQ. ID. No. 3)

```
  1 mrecisvhvg qagvqmgnac welyclehgi qpdgqmpsdk tigggddsft tffcetgagk
 61 hvpravfvdl eptvideirn gpyrqlfhpe qlitgkedaa nnyarghyti gkeiidpvld
121 rirklsdqct glqgflvfhs fgggtgsgft sllmerlsvd ygkksklefs iypapqvsta
181 vvepynsilt thttlehsdc afmvdneaiy dicrrnldie rptytnlnrl isqivssita
241 slrfdgalnv dltefqtnlv pyprihfpla tyapvisaek ayheqlsvae itnacfepan
301 qmvkcdprhg kymaccllyr gdvvpkdvna aiaaiktkrs iqfvdwcptg fkvginyqpp
361 tvvpggdlak vqravcmlsn ttaiaeawar ldhkfdlmya krafvhwyvg egmeegefse
421 aredmaalek dyeevgidsy ededegee
```

Figure 12

Tubulin alpha-8 chain isoform 1 [Homo sapiens]

(SEQ. ID. No. 4)

```
  1 mrecisvhvg qagvqignac welfclehgi qadgtfdaqa skindddsft tffsetgngk
 61 hvpravmidl eptvvdevra gtyrqlfhpe qlitgkedaa nnyarghytv gkesidlvld
121 rirkltdacs glqgflifhs fgggtgsgft sllmerlsld ygkksklefa iypapqvsta
181 vvepynsilt thttlehsdc afmvdneaiy dicrrnldie rptytnlnrl isqivssita
241 slrfdgalnv dltefqtnlv pyprihfplv tyapiisaek ayheqlsvae itsscfepns
301 qmvkcdprhg kymaccmlyr gdvvpkdvnv aiaaiktkrt iqfvdwcptg fkvginyqpp
361 tvvpggdlak vqravcmlsn ttaiaeawar ldhkfdlmya krafvhwyvg egmeegefse
421 aredlaalek dyeevgtdsf eenegeef
```

Figure 13

Tubulin beta chain [Homo sapiens] (SEQ. ID. No. 5)

```
  1 mreivhiqag qcgnqigakf wevisdehgi dptgtyhgds dlqldrisvy yneatggkyv
 61 prailvdlep gtmdsvrsgp fgqifrpdnf vfgqsgagnn wakghytega elvdsvldvv
121 rkeaescdcl qgfqlthslg ggtgsgmgtl liskireeyp drimntfsvv pspkvsdtvv
181 epynatlsvh qlventdety cidnealydi cfrtlklttp tygdlnhlvs atmsgvttcl
241 rfpgqlnadl rklavnmvpf prlhffmpgf apltsrgsqq yraltvpelt qqvfdaknmm
301 aacdprhgry ltvaavfrgr msmkevdeqm lnvqnknssy fvewipnnvk tavcdipprg
361 lkmavtfign staiqelfkr iseqftamfr rkaflhwytg egmdemefte aesnmndlvs
421 eyqqyqdata eeeedfgeea eeea
```

Figure 14

Tubulin beta-3 chain isoform 1 [Homo sapiens] (SEQ. ID. No. 6)

```
  1 mreivhiqag qcgnqigakf wevisdehgi dpsgnyvgds dlqlerisvy yneasshkyv
 61 prailvdlep gtmdsvrsga fghlfrpdnf ifgqsgagnn wakghytega elvdsvldvv
121 rkecencdcl qgfqlthslg ggtgsgmgtl liskvreeyp drimntfsvv pspkvsdtvv
181 epynatlsih qlventdety cidnealydi cfrtlklatp tygdlnhlvs atmsgvttsl
241 rfpgqlnadl rklavnmvpf prlhffmpgf apltargsqq yraltvpelt qqmfdaknmm
301 aacdprhgry ltvatvfrgr msmkevdeqm laiqsknssy fvewipnnvk vavcdipprg
361 lkmsstfign staiqelfkr iseqftamfr rkaflhwytg egmdemefte aesnmndlvs
421 eyqqyqdata eeegemyedd eeeseaqgpk
```

USE OF ACETYLATED TUBULIN AS A BIOMARKER OF DRUG RESPONSE TO FURAZANOBENZIMIDAZOLES

This application is a National Stage Application of PCT/EP2012/052954 filed Feb. 21, 2012, which claims priority from European Patent Application 11155774.0 filed on Feb. 24, 2011. The priority of both said PCT and European Patent Application are claimed.

The present invention relates to use of acetylated tubulin as a biomarker for predicting the response of a disease, such as a neoplastic or autoimmune disease, preferably cancer, to a compound of general formula I, such as 3-(4-{1-[2-(4-amino-phenyl)-2-oxo-ethyl]-1H-benzoimidazol-2-yl}-furazan-3-ylamino)-propionitrile (BAL27862). In other aspects it relates to methods and kits, as well as methods of treatment involving the use of the biomarker.

Microtubules are one of the components of the cell cytoskeleton and are composed of heterodimers of alpha and beta tubulin. Agents that target microtubules are among the most effective cytotoxic chemotherapeutic agents having a broad spectrum of activity. Microtubule destabilising agents (e.g. the vinca-alkaloids such as vincristine, vinblastine and vinorelbine) are used for example in the treatment of several types of hematologic malignancies, such as lymphoblastic leukaemia and lymphoma, as well as solid tumours, such as lung cancer. Microtubule stabilising agents (e.g. the taxanes such as paclitaxel, docetaxel) are used for example in the treatment of solid tumours, including breast, lung and prostate cancer.

However resistance to these known microtubule targeting agents can occur. The resistance can either be inherent or can be acquired after exposure to these agents. Such resistance therefore impacts patient survival rates, as well as choices of treatment regimes. Several potential mechanisms of resistance have been identified, and include defects in the microtubule targets, such as elevated levels of beta-tubulin subtype III and acquired mutations in beta-tubulin subtype I that are known to reduce taxane binding. Furthermore, defects in other cell proteins have been suggested to be associated with resistance to certain microtubule targeting agents, such as overexpression of the efflux pump P-glycoprotein (P-gp pump, also known as multi-drug resistance protein 1 or MDR1). Such factors may then be used as biomarkers of resistance to these conventional microtubule targeting agents.

A relatively recently discovered class of microtubule destabilising agents are compounds encompassed by the formula given below:
wherein

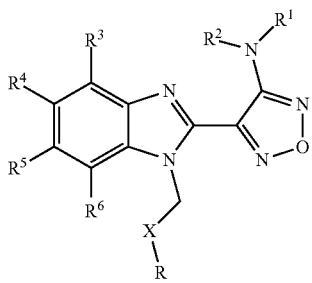

(I)

R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y, wherein Y stands for oxygen or nitrogen substituted by hydroxy or lower alkoxy;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable salts thereof;
or wherein
R represents phenyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;
and wherein pyridinyl is optionally substituted by lower alkoxy, amino or halogen;
X represents oxygen;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable salts thereof;
and wherein the prefix lower denotes a radical having up to and including a maximum of 7, especially up to and including a maximum of 4 carbon atoms.

These compounds are disclosed in WO2004/103994 A1, which is incorporated by cross-reference herein. These compounds have been shown to arrest tumour cell proliferation and induce apoptosis.

The synthesis of compounds of formula I is described in WO2004/103994 A1, in general on pages 29-35, and specifically on pages 39-55, which are incorporated herein by cross-reference. They may be prepared as disclosed or by an analogous method to the processes described therein.

One compound falling within this class, known as BAL27862, and shown in WO2004/103994 A1 as example 58, and specifically incorporated by reference herein, has the structure and chemical name given below:

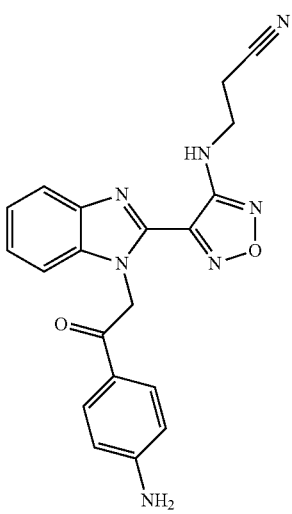 [SMILES: N#CCCNc1nonc1-c1nc2ccccc2n1CC(=O)c1ccc(N)cc1]

Chemical name: 3-(4-{1-[2-(4-Amino-phenyl)-2-oxo-ethyl]-1H-benzoimidazol-2-yl}-furazan-3-ylamino)-propionitrile; or herein as Compound A Further compounds exemplified in WO2004/103994 A1 as examples 50 and 79 respectively, and also specifically incorporated by cross-reference herein, have the structures and chemical names given below:

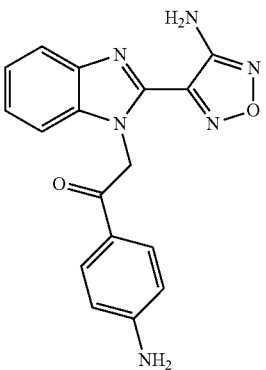 [SMILES: Nc1ccc(C(=O)Cn2c(-c3nonc3N)nc3ccccc32)cc1]

Chemical name: 2-[2-(4-Amino-furazan-3-yl)-benzoimidazol-1-yl]-1-(4-amino-phenyl)-ethanone; or herein as Compound B
and

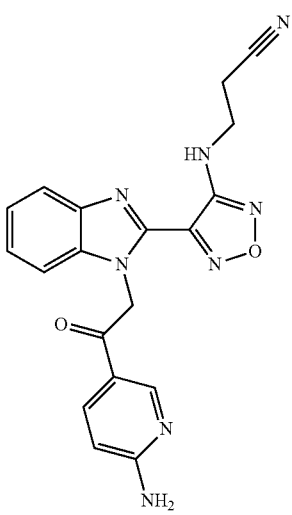 [SMILES: N#CCCNc1nonc1-c1nc2ccccc2n1CC(=O)c1ccc(N)nc1]

Chemical name: 3-(4-{1-[2-(6-Amino-pyridin-3-yl)-2-oxo-ethyl]-1H-benzoimidazol-2-yl}-furazan-3-ylamino)-propionitrile; or herein as Compound C.

BAL27862 has activity across a broad panel of experimental, solid tumour xenograft models. Moreover, activity is retained even against tumour models which were selected for resistance to conventional microtubule targeting agents (including the vinca-alkaloid microtubule destabilisers and the microtubule stabilisers paclitaxel and epothilone B). BAL27862 activity is not affected by over-expression of the P-gp pump in any models tested in vitro, nor in human mammary tumour xenografts. Additionally, BAL27862 retained its activity despite elevated levels of beta-tubulin subtype III and mutations in tubulin subtype I.

Hence, BAL27862 activity is not affected by a number of factors that confer resistance to conventional microtubule targeting agents.

Moreover, it is known that compounds of general formula I have a different effect on the phenotype of cells compared to other microtubule targeting agents, including other microtubule destabilisers. Treatment with a compound of general formula I induces a consistent microtubule phenotype in tumour cell lines derived from a variety of organs, for example lung, cervix and breast, as seen in FIG. 1. Staining the microtubules in these cells with an anti alpha tubulin antibody shows that rather than the mitotic spindle fibres of untreated cells, only dot-like structures are visible in the treated cells. This same effect is also shown using Compounds C and B in FIGS. 2A and 2B respectively on the lung cancer cell line A549. It is however very distinct from that observed with the conventional microtubule targeting agents vinblastine, colchicine, paclitaxel and nocodazole as seen in FIGS. 3B, 3C, 3D and 4, respectively. The microtubules were stained with an anti-alpha tubulin antibody and the cells viewed at a 1000× magnification (FIGS. 3, 4). For the cells treated with BAL27862, multiple dot-like structures are visible, whereas, in stark contrast, the other conventional drugs produce filamentous microtubule structures, or dense microtubule aggregate structures. These differences at the phenotypic level, at compound doses considered optimal in terms of antiproliferative effect, indicate a difference in the mode of action at the molecular level.

Furthermore, it is known that BAL27862 elicits a dominant microtubule phenotype in the presence of the other microtubule targeting agents. Treatment with vinblastine, colchicine, paclitaxel or nocodazole alone induced the microtubule phenotypes characteristic of these agents (FIG. 5A, 5D, 5G, 6C-6F respectively). However, combination treatment with BAL27862 for the last 4 hours resulted in disruption of these phenotypes; despite the continued presence of vinblastine, colchicine, paclitaxel or nocodazole (FIG. 5B, 5E, 5H, 6G-6J respectively). In contrast, treating first with BAL27862 and subsequently for 4 hours in combination with vinblastine, colchicine, paclitaxel or nocodazole had no impact on generation of the phenotype consistent with BAL27862 treatment (FIG. 5C, 5F, 5I, 6K-6N respectively).

These data all demonstrate that BAL27862 affects microtubule biology in a different manner than conventional microtubule targeting agents.

Thus, from information about conventional microtubule targeting agents, predictions cannot be made concerning if, or how, particular genes are involved in the action of compounds of formula I.

An object of the present invention is to identify factors which are associated with response to compounds of formula I or pharmaceutically acceptable derivatives thereof, for example to identify factors associated with resistance to compounds of general formula I, in particular BAL27862 or pharmaceutically acceptable derivatives thereof, as defined below.

It has surprisingly been found that acetylated tubulin may be used as a biomarker of response to treatment with a compound of general formula I or pharmaceutically acceptable derivatives thereof, as defined below.

In one preferred embodiment of the invention, relatively high acetylated tubulin levels in a tumour sample are associated with resistance to BAL27862, as described below.

Tubulin is subjected to a variety of post-translational modifications, including detyrosination/tyrosination, acetylation, glutamylation, polyglycylation, phosphorylation of serine residues and phosphorylation of tyrosine residues, making it one of the most modified proteins known.

The acetylation and deacetylation of lysines in tubulin is known to occur, although the exact function of these changes has yet to be elucidated. The best characterised site of acetylation is on the alpha tubulin lysine 40, however additional acetylation sites have been identified on both alpha and beta tubulin. To date two microtubule deacetylases have been identified: histone deacetylase 6 (HDAC6) and Sirtuin T2 (SirT2). Very recently alphaTAT1 and the Elp3 subunit of the Elongator complex were identified as lysine 40 tubulin acetyltransferases. Furthermore, the protein known as San reportedly has lysine 252 beta-tubulin acetyltransferase activity. (*A novel acetylation of beta-tubulin by San modulates microtubule polymerization via down regulating tubulin incorporation*, Chih-Wen Chu et al., Mol Biol Cell. 2010, Dec. 22.)

Acetylated tubulin is also known as acetylated-tubulin, acetylated microtubule(s), or acetyl tubulin, and the term acetylated tubulin shall be used herein to also encompass these synonyms. The designation acetylated tubulin, shall also encompass forms wherein other post-translational modifications may additionally be present. The alpha and beta tubulin which form the basis for the acetylated tubulin are known to exist in multiple variants, subtypes and isoforms, as well as there being multiple alpha and beta tubulin genes which give rise to these. Preferably the tubulin which is acetylated relates to human variants, subtypes and isoforms of alpha and beta tubulin, more preferably to human variants, subtypes and isoforms of alpha tubulin. Subtypes of alpha tubulin include, but are not limited to, tubulin alpha 1A, tubulin alpha 1B, tubulin alpha 1C, tubulin alpha 2, tubulin alpha 3C/D, tubulin alpha 4A, and tubulin alpha-8 chain isoform 1. The subtypes tubulin alpha 1A, tubulin alpha 1B, tubulin alpha 1C, tubulin alpha 2, tubulin alpha 3C/D and tubulin alpha 4A possess a lysine 40 and are thus a preferred subset of alpha tubulins according to the invention. Subtypes of beta tubulin include, but are not limited to, tubulin beta chain, tubulin beta-1 chain and tubulin beta-3 chain isoform 1. The protein sequences of the alpha tubulin subtypes are accessible via the following National Center for Biotechnology Information (NCBI) Reference numbers NP_006000, NP_006073, NP_116093, ABD72607, NP_005992, NP_005991 and NP_061816, and the beta tubulin subtypes are accessible via NP_821133, NP_110400 and NP_006077 respectively. In an alternatively preferred embodiment the tubulin which is acetylated is selected from the group consisting of tubulin alpha-1C (NP_116093.1), tubulin alpha 3C/D (NP_005992.1), tubulin alpha-4A (NP_005991.1) tubulin alpha-8 chain isoform 1 (NP_061816.1), tubulin beta chain (NP_821133.1) and tubulin beta-3 chain isoform 1 (NP_006077.2). The polypeptide sequences of these are also listed in FIGS. 9-14 as SEQ ID NO. 1-6, respectively. Particularly preferably the tubulin which is acetylated is selected from the group consisting of tubulin alpha-1C, tubulin alpha 3C/D, tubulin alpha-4A and tubulin alpha-8 chain isoform 1. More particularly preferably the tubulin which is acetylated is selected from the group consisting of tubulin alpha-1C, tubulin alpha 3C/D and tubulin alpha-4A.

One aspect of the present invention relates to use of acetylated tubulin as a biomarker for predicting the response to a compound, wherein the compound is a compound of general formula I,

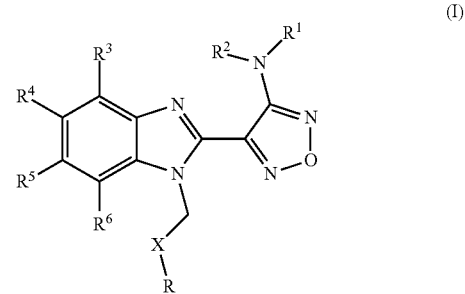

(I)

wherein
R represents phenyl, thienyl or pyridinyl
  wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y, wherein Y stands for oxygen or nitrogen substituted by hydroxy or lower alkoxy;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable derivatives thereof,
or wherein
R represents phenyl or pyridinyl
  wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;

X represents oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof;

and wherein the prefix lower denotes a radical having up to and including a maximum of 7, especially up to and including a maximum of 4 carbon atoms.

Preferably the response may be of a disease in a subject. Also preferably the response may be to treatment, i.e. to treatment with the compound of general formula I or pharmaceutically acceptable derivatives thereof.

The biomarker acetylated tubulin is measured ex vivo in a sample or samples taken from the human or animal body, preferably taken from the human body.

In a preferred embodiment, the invention relates to use of acetylated tubulin as a biomarker for predicting the resistance of a disease in a subject to a compound of general formula I or pharmaceutically acceptable derivatives thereof as defined above.

Preferably the pharmaceutically acceptable derivative is selected from the group consisting of a salt, solvate, pro-drug, salt of a pro-drug, polymorph and isomer of a compound of general formula I as defined above. Pro-drugs are preferably ester and amides of naturally occurring amino acids, small peptides or pegylated hydroxy acids. More preferably, the pro-drug is an amide formed from an amino group present within the R group of the compound of general formula I and the carboxy group of glycine, alanine or lysine.

Particularly preferably the compound is

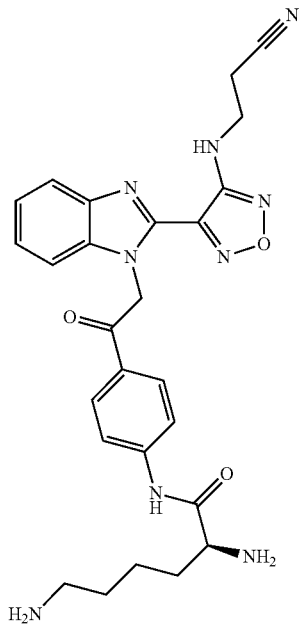

or a pharmaceutically acceptable salt thereof, preferably a hydrochloride salt, most preferably a dihydrochloride salt thereof.

Another aspect of the present invention relates to a method for predicting the response of a disease in a subject to a compound of general formula I or pharmaceutically acceptable derivatives thereof as defined above, comprising the steps of:
a) measuring a level of acetylated tubulin in a sample pre-obtained from the subject to obtain a value or values representing this level; and
b) comparing the value or values from step a) to a standard value or set of standard values or to pre-treatment initiation levels.

Further preferably the response which is to be predicted is resistance.

The measuring of a level or levels of acetylated tubulin is performed ex vivo in a sample or samples pre-obtained from the subject. Pre-obtained refers to the fact that the sample is obtained before it is subjected to any method involving measuring the level of the biomarker, and pre-obtained is not to be understood as in relation to treatment.

In a preferred embodiment, a higher level of acetylated tubulin in the sample from the subject relative to the standard value or set of standard values or pre-treatment initiation levels predicts resistance.

Also preferably, the disease is a neoplastic or autoimmune disease. More preferably the disease is cancer. Especially preferably, the cancer is selected from the group consisting of breast cancer, prostate cancer, cervical cancer, ovarian cancer, gastric cancer, colorectal cancer (i.e. including colon cancer and rectal cancer), pancreatic cancer, liver cancer, brain cancer, neuroendocrine cancer, lung cancer, kidney cancer, hematological malignancies, melanoma, T-cell leukemia, and sarcomas. More especially preferably the cancer is selected from the group consisting of breast cancer, cervical cancer, ovarian cancer, T-cell leukemia and lung cancer. In an especially preferred embodiment the cancer is selected from the group consisting of lung cancer, ovarian cancer and T-cell leukemia.

In a further aspect, the invention relates to a method of treating a neoplastic or autoimmune disease, preferably cancer, in a subject in need thereof, comprising measuring a level of acetylated tubulin in a sample from the subject to obtain a value or values representing this level, and treating the subject with a compound of general formula I or a pharmaceutically acceptable derivative thereof as defined above, if the level of acetylated tubulin in said sample is not higher than a standard value or set of standard values or pre-treatment initiation levels.

In yet a further aspect, the invention relates to acetylated tubulin for use in the treatment of a neoplastic or autoimmune disease, preferably cancer, comprising measuring a level of acetylated tubulin in a sample from the subject to obtain a value or values representing this level, and treating the subject with a compound of general formula I or a pharmaceutically acceptable derivative thereof as defined above, if the level of acetylated tubulin is not higher than a standard value or set of standard values or pre-treatment initiation levels.

The measuring of a level of acetylated tubulin is performed ex-vivo in a sample pre-obtained from the subject.

The invention also relates in another aspect to a method of treating a neoplastic or autoimmune disease, preferably cancer, by first decreasing the level of acetylated tubulin in a subject that has a sample with a higher level of acetylated tubulin compared to a standard level or set of standard levels or pre-treatment initiation levels, then treating the subject with a compound of general formula I or a pharmaceutically acceptable derivative thereof as defined above.

In yet another aspect the invention relates to a kit for predicting the response to a compound of general formula I or a pharmaceutically acceptable derivative thereof, as defined above, comprising reagents necessary for measuring a level of acetylated tubulin in a sample. More preferably the kit also comprises a comparator module which comprises a standard value or set of standard values to which the level of acetylated tubulin in the sample is compared.

Furthermore preferably the kit comprises a compound of general formula I or a pharmaceutically acceptable derivative thereof as defined above. In an especially preferred embodiment the kit comprises a compound of the following formula or a pharmaceutically acceptable salt thereof.

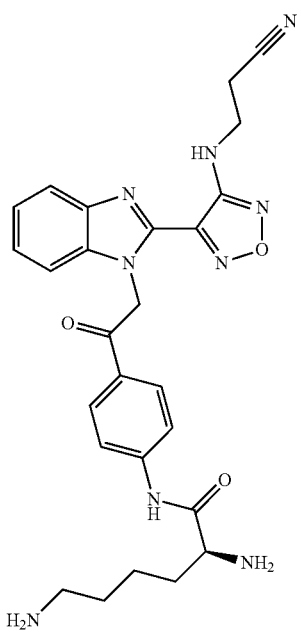

Chemical name: S-2,6-Diamino-hexanoic acid [4-(2-{2-[4-(2-cyano-ethylamino)-furazan-3-yl]-benzoimidazol-1-yl}-acetyl)-phenyl]-amide In a particularly preferred embodiment the pharmaceutically acceptable salt is a dihydrochloride salt.

Another further aspect of the invention relates to a device for predicting the response to a compound of general formula I or a pharmaceutically acceptable derivative thereof as defined above, comprising reagents necessary for measuring a level of acetylated tubulin in a sample and a comparator module comprising a standard value or set of standard values to which the level of acetylated tubulin in the sample is compared.

In a preferred embodiment, the reagents in the kit or device comprise a capture reagent comprising a detector for acetylated tubulin, and a detector reagent. Especially preferably the capture reagent is an antibody. Also preferably, the disease is predicted to be resistant to treatment with said compound when acetylated tubulin is higher relative to a standard value or set of standard values or pre-treatment initiation levels. In a preferred embodiment, the comparator module is included in instructions for use of the kit. In another preferred embodiment the comparator module is in the form of a display device.

Embodiments of the present invention will now be described by way of example with reference to the accompanying figures. The invention however is not to be understood as limited to these embodiments.

BRIEF DESCRIPTION OF THE FIGURES

FIGS. 1A and 1B: A549 NSCLC cells;
FIGS. 1C and 1D: HeLa cervical cancer cells;
FIGS. 1E and 1F: SKBR3 breast cancer cells
Vehicle control treatment:
FIGS. 1A, 1C & 1E,
BAL27862 treatment:
FIGS. 1B, 1D & 1F.
FIG. 2A: treatment with 20 nM Compound C
FIG. 2B: treatment with 80 nM Compound B
FIG. 5A: 24 hours vinblastine treatment;
FIG. 5B: 24 hours vinblastine treatment with the final 4 hours including BAL27862;
FIG. 5C: 24 hours BAL27862 treatment with the final 4 hours including vinblastine.
FIG. 5D: 24 hours colchicine treatment;
FIG. 5E: 24 hours colchicine treatment with the final 4 hours including BAL27862;
FIG. 5F: 24 hours BAL27862 treatment with the final 4 hours including colchicine.
FIG. 5G: 24 hours paclitaxel treatment;
FIG. 5H: 24 hours paclitaxel treatment with the final 4 hours including BAL27862;
FIG. 5I: 24 hours BAL27862 treatment with the final 4 hours including paclitaxel.

FIG. 6A: 24 hours control treatment;

FIG. 6B: 24 hours of 25 nM BAL27862 treatment;

FIG. 6C: 24 hours of 50 nM nocodazole treatment

FIG. 6D: 24 hours of 100 nM nocodazole treatment

FIG. 6E: 24 hours of 150 nM nocodazole treatment

FIG. 6F: 24 hours of 200 nM nocodazole treatment

FIG. 6G: 24 hours of 50 nM nocodazole treatment with the final 4 hours including 25 nM BAL27862;

FIG. 6H: 24 hours of 100 nM nocodazole treatment with the final 4 hours including 25 nM BAL27862;

FIG. 6I: 24 hours of 150 nM nocodazole treatment with the final 4 hours including 25 nM BAL27862;

FIG. 6J: 24 hours of 200 nM nocodazole treatment with the final 4 hours including 25 nM BAL27862;

FIG. 6K: 24 hours of 25 nM BAL27862 treatment with the final 4 hours including 50 nM nocodazole;

FIG. 6L: 24 hours of 25 nM BAL27862 treatment with the final 4 hours including 100 nM nocodazole;

FIG. 6M: 24 hours of 25 nM BAL27862 treatment with the final 4 hours including 150 nM nocodazole;

FIG. 6N: 24 hours of 25 nM BAL27862 treatment with the final 4 hours including 200 nM nocodazole.

FIG. 9: Shows the protein sequence of tubulin alpha-1C chain [Homo sapiens] (SEQ. ID. No. 1)

FIG. 10: Shows the protein sequence of tubulin alpha-3C/D chain [Homo sapiens] (SEQ ID No. 2)

FIG. 11: Shows the protein sequence of tubulin alpha-4A chain [Homo sapiens] (SEQ. ID. NO. 3)

FIG. 12: Shows the protein sequence of tubulin alpha-8 chain isoform 1 [Homo sapiens] (SEQ. ID. NO. 4)

FIG. 13: Shows the protein sequence of tubulin beta chain [Homo sapiens] (SEQ. ID. No. 5)

FIG. 14: Shows the protein sequence of tubulin beta-3 chain isoform 1 [Homo sapiens] (SEQ. ID. NO. 6)

DETAILED DESCRIPTION

Compounds of Formula I

Figure 1:
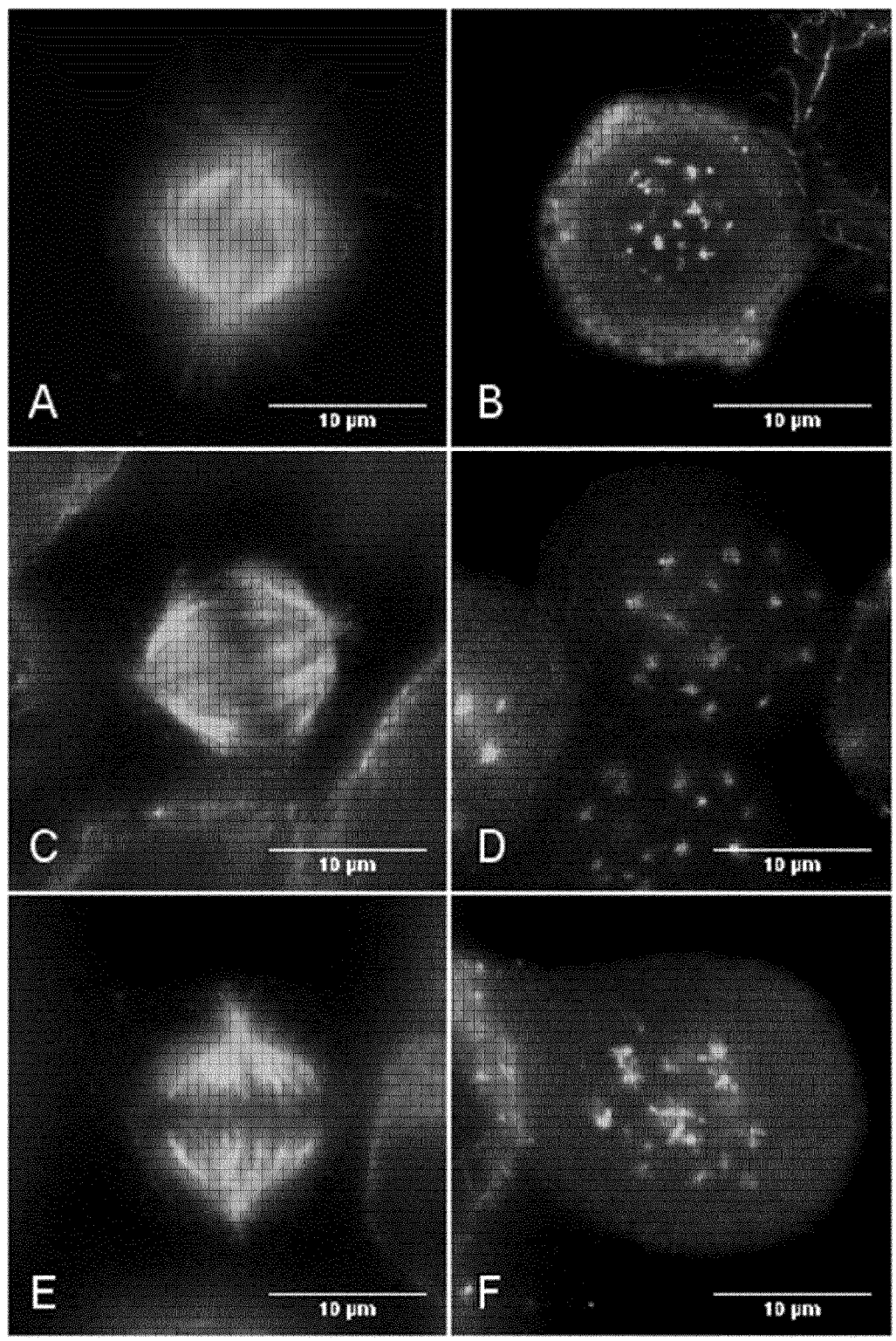
FIG. 1: Shows the treatment of human tumour cell lines from different histotypes with 50 nM BAL27862. The microtubules of mitotic or G2/M arrested cells were stained after 24 hours treatment with 50 nM BAL27862 or vehicle control.

The compounds according to the invention are represented by general formula I:

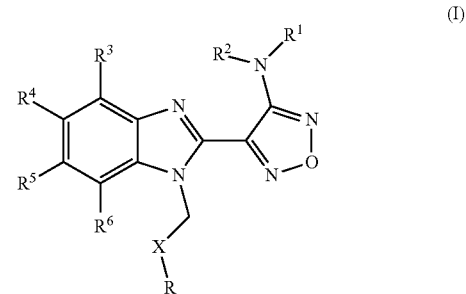

(I)

wherein

R represents phenyl, thienyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof, or wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;
X represents oxygen
R¹ represents hydrogen, lower alkylcarbonyl, hydroxy-lower alkyl or cyano-lower alkyl;
R², R³ and R⁶ represent hydrogen;
R⁴ and R⁵, independently of each other, represent hydrogen, lower alkyl or lower alkoxy;
or R⁴ and R⁵ together represent methylenedioxy;
and pharmaceutically acceptable derivatives thereof;
and wherein the prefix lower denotes a radical having up to and including a maximum of 7, especially up to and including a maximum of 4 carbon atoms.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl and tetrahydropyranyl.

Acyl designates, for example, alkylcarbonyl, cyclohexyl-carbonyl, arylcarbonyl, aryl-lower alkylcarbonyl, or heteroarylcarbonyl. Lower acyl is preferably lower alkylcarbonyl, in particular propionyl or acetyl.

Preferably, the compound of general formula I according to the invention is defined as wherein R¹ is selected from the group consisting of hydrogen, acetyl, CH₂CH₂CN and CH₂CH₂CH₂OH.

In one preferred embodiment, the compound of general formula I according to the invention is selected from the group consisting of:
4-(1-Phenacyl-1H-benzimidazol-2-yl)-furazan-3-ylamine,
4-[1-(4-Bromophenacyl)-1H-benzimidazol-2-yl]-furazan-3-ylamine oxime,
N-{4-[1-(4-Chlorophenacyl)-1H-benzimidazol-2-yl]-furazan-3-yl}-acetamide,
4-[1-(4-Chlorophenacyl)-1H-benzimidazol-2-yl]-furazan-3-yl-N-(2-cyanoethyl)-amine
4-[1-(4-Chlorophenacyl)-1H-benzimidazol-2-yl]-furazan-3-yl-N-(3-hydroxypropyl)-amine,
4-[1-(3-Amino-4-chlorophenacyl)-1H-benzimidazol-2-yl]-furazan-3-ylamine
4-[1-(3-Methoxy-4-methoxymethoxy-phenacyl)-1H-benzimidazol-2-yl]-furazan-3-ylamine,
and pharmaceutically acceptable derivatives thereof.

In another preferred embodiment, the compound of general formula I according to the invention is selected from the group consisting of:

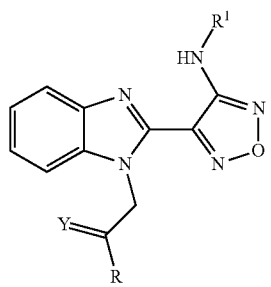

wherein
R, Y and R¹ are defined as follows:

| R | Y | R¹ |
|---|---|---|
| 4-Cl-C₆H₄ | O | H |
| C₆H₅ | NOH | H |
| C₆H₅ | NOMe | H |
| 4-MeO-C₆H₄ | O | H |
| 4-MeO-C₆H₄ | NOH | H |
| 4-Cl-C₆H₄ | NOH | H |
| 4-Cl-C₆H₄ | NOMe | H |
| 3-MeO-C₆H₄ | O | H |
| 3-MeO-C₆H₄ | NOH | H |
| 3-MeO-C₆H₄ | NOMe | H |
| 4-Ph-C₆H₄ | O | H |
| 4-Ph-C₆H₄ | NOH | H |
| 4-Ph-C₆H₄ | NOMe | H |

-continued

| R | Y | R¹ |
|---|---|---|
| 4-Br-C₆H₄ | O | H |
| 4-Br-C₆H₄ | NOMe | H |
| 2,4-diCl-C₆H₃ | O | H |
| 2-Cl-C₆H₄ | O | H |
| 2-Cl-C₆H₄ | NOH | H |
| 2-Cl-C₆H₄ | NOMe | H |
| 3-Cl-C₆H₄ | O | H |
| 3-Cl-C₆H₄ | NOH | H |
| 3-Cl-C₆H₄ | NOMe | H |
| 4-MeO-C₆H₄ | NOMe | H |
| 4-Et₂N-C₆H₄ | O | H |
| C₆H₅ | O | Ac |
| 4-F₃C-C₆H₄ | O | H |

-continued

| R | Y | R¹ |
|---|---|---|
| 4-Me-C₆H₄ | O | H |
| 3,4-methylenedioxy-C₆H₃ | O | H |
| 4-Br-C₆H₄ | O | CH₂CH₂CN |
| 4-MeO-C₆H₄ | O | CH₂CH₂CN |
| 4-O₂N-C₆H₄ | O | H |
| 4-H₂N-C₆H₄ | O | H |
| 3,4-diMe-C₆H₃ | O | CH₂CH₂CH₂OH |
| 3,4-diMe-C₆H₃ | O | H |
| 3,4-diMe-C₆H₃ | O | CH₂CH₂CN |
| 4-Et-C₆H₄ | O | H |
| 4-Et-C₆H₄ | O | CH₂CH₂CN |
| 4-O₂N-C₆H₄ | O | CH₂CH₂CN |
| 4-H₂N-C₆H₄ | O | CH₂CH₂CN |

-continued

| R | Y | R¹ |
|---|---|---|
| 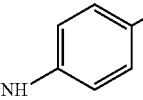 | O | H |
| 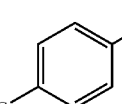 | O | H |
| 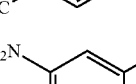 | O | H |
| 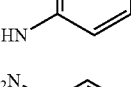 | O | H |
| 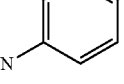 | O | H |
| 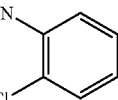 | O | H |
| 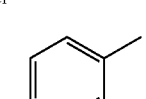 | O | H |
| 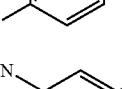 | O | H |
| 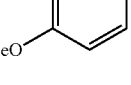 | O | CH₂CH₂CN |
| 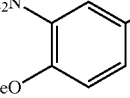 | O | H |
| 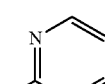 | O | H |
| 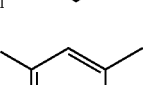 | O | H |
| 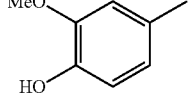 | O | H |

-continued

| R | Y | R¹ |
|---|---|---|
| 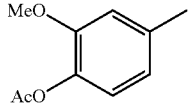 | O | H |
| 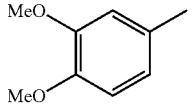 | O | H |
| 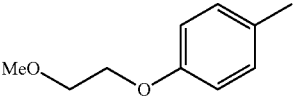 | O | H |
| 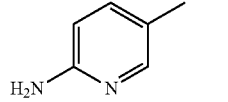 | O | H |
| 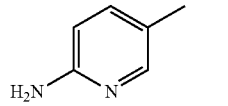 | O | H |
| 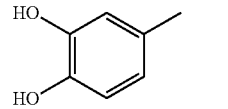 | O | CH₂CH₂CN |
| 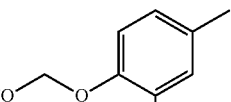 | O | H |
| 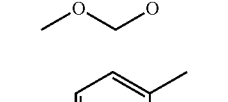 | O | H |
| 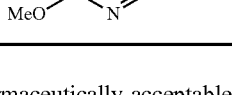 | O | CH₂CH₂CN | or pharmaceutically acceptable derivatives thereof.

In yet another preferred embodiment, the compound of general formula I according to the invention is selected from the group consisting of:

4-(1-Phenoxymethyl-1H-benzimidazol-2-yl)-furazan-3-ylamine,

4-[1-(4-Fluorophenoxymethyl)-1H-benzimidazol-2-yl]-furazan-3-ylamine,

4-[1-(3,4-Dimethylphenoxymethyl)-1H-benzimidazol-2-yl]-furazan-3-yl-N-(2-cyanoethyl)-amine and compounds represented by the formula:

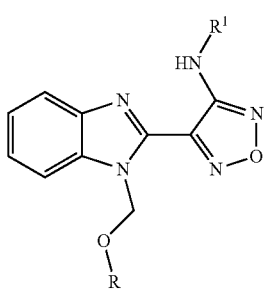
wherein R and R¹ are as defined below
| R | R¹ |
|---|---|
| 4-Cl-C₆H₄ | H |
| 4-Br-C₆H₄ | H |
| 4-MeO-C₆H₄ | H |
| 4-F₃C-C₆H₄ | H |
| 3,4-diCl-C₆H₃ | H |
| 4-Cl-C₆H₄ | CH₂CH₂CN |
| 4-Br-C₆H₄ | CH₂CH₂CN |
| C₆H₅ | CH₂CH₂CN |
| 4-OHC-C₆H₄ | H |
| 4-HOCH₂-C₆H₄ | H |
| 4-O₂N-C₆H₄ | H |
| 4-H₂N-C₆H₄ | H |
| 4-H₂N-C₆H₄ | H |
| 3,4-diMe-C₆H₃ | H |
| 3,5-bis(CF₃)-C₆H₃ | H |
| 3-F₃C-C₆H₄ | H |
| 4-Me-C₆H₄ | CH₂CH₂CN |
| 3,4-diMe-C₆H₃ | CH₂CH₂CH₂OH |
| 6-Cl-pyridin-3-yl | H |
| 6-H₂N-pyridin-3-yl | H |
and pharmaceutically acceptable derivatives thereof.

In still yet another preferred embodiment the compound of general formula I according to the invention is:

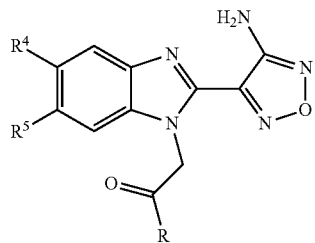

wherein R, R⁴ and R⁵ are as defined below

| R | R⁴ | R⁵ |
|---|----|----|
| phenyl | Me | Me |
| 4-Br-phenyl | Me | Me |
| 4-Cl-phenyl | Me | Me |
| 4-MeO-phenyl | Me | Me |
| 4-Ph-phenyl | Me | Me |
| phenyl | OMe | OMe |
| 4-Cl-phenyl | OMe | OMe |
| 4-Br-phenyl | OMe | OMe |
| 4-MeO-phenyl | OMe | OMe |
| 4-Ph-phenyl | OMe | OMe | or pharmaceutically acceptable derivatives thereof.

More preferably, the compound according to the invention is a compound of general formula I

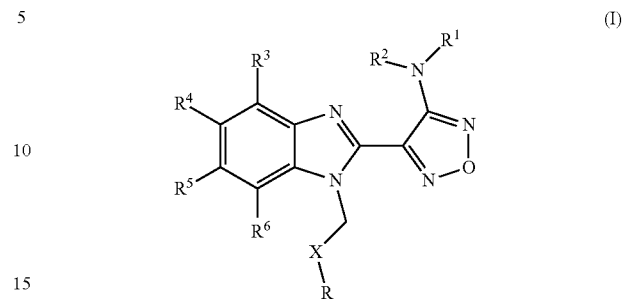

wherein
R represents phenyl or pyridinyl
  wherein phenyl is optionally substituted by one or two substituents independently selected from lower alkyl, lower alkoxy, amino, acetylamino, halogen and nitro;
  and wherein pyridinyl is optionally substituted by amino or halogen;
X represents a group C=O;
R¹ represents hydrogen or cyano-lower alkyl;
R², R³, R⁴, R⁵ and R⁶ represent hydrogen;
and pharmaceutically acceptable derivatives thereof,
and wherein the prefix lower denotes a radical having up to and including a maximum of 7, especially up to and including a maximum of 4 carbon atoms.

Especially preferably, the compound according to the invention is represented by the following formula

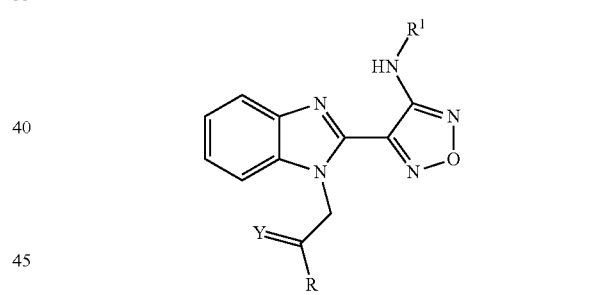

wherein R, Y and R¹ are defined as follows:

| R | Y | R¹ |
|---|---|----|
| 4-H₂N-phenyl | O | H |
| 4-H₂N-phenyl | O | CH₂CH₂CN |
| 6-H₂N-pyridin-3-yl | O | H |

| R | Y | R¹ |
|---|---|---|
| 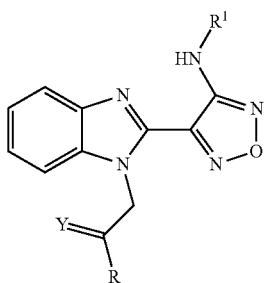 | O | CH₂CH₂CN | or pharmaceutically acceptable derivatives thereof.

More especially preferably, the compound according to the invention is represented by the following formula

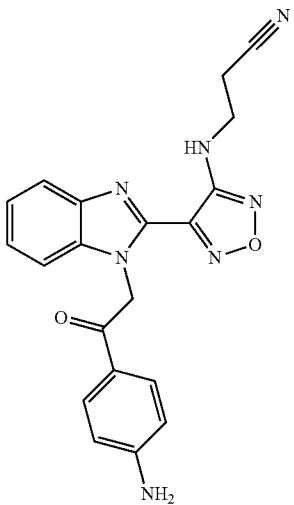

wherein R, Y and R1 are defined as follows:

| R | Y | R¹ |
|---|---|---|
| H₂N—⟨phenyl⟩— | O | CH₂CH₂CN |
| H₂N—⟨phenyl⟩— | O | H |
| H₂N—⟨pyridyl⟩— | O | CH₂CH₂CN | or pharmaceutically acceptable derivatives thereof.

Particularly preferably, the compound according to the invention is

[structure shown]

or pharmaceutically acceptable derivatives thereof.

The term derivative or derivatives in the phrase "pharmaceutically acceptable derivative" or "pharmaceutically acceptable derivatives" of compounds of general formula I relates to salts, solvates and complexes thereof and to solvates and complexes of salts thereof, as well as to pro-drugs, polymorphs, and isomers thereof (including optical, geometric and tautomeric isomers) and also salts of pro-drugs thereof. In a more preferred embodiment, it relates to salts and pro-drugs, as well as to salts of pro-drugs thereof.

Salts are preferably acid addition salts. Salts are formed, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The compound according to the invention may be administered in the form of a pro-drug which is broken down in the human or animal body to give a compound of the formula I. Examples of pro-drugs include in vivo hydrolysable esters and amides of a compound of the formula I. Particular pro-drugs considered are ester and amides of naturally occurring amino acids and ester or amides of small peptides, in particular small peptides consisting of up to five, preferably two or three amino acids as well as esters and amides of pegylated hydroxy acids, preferably hydroxy acetic acid and lactic acid. Pro-drug esters are formed from the acid function of the amino acid or the C terminal of the peptide and suitable hydroxy group(s) in the compound of formula I. Pro-drug amides are formed from the amino function of the amino acid or the N terminal of the peptide and suitable carboxy group(s) in the compound of formula I, or from the acid function of the amino acid or the C terminal of the peptide and suitable amino group(s) in the compound of formula I. Particularly preferably the pro-drug amides are formed from the amino group(s) present within the R group of formula I.

More preferably, the pro-drug is formed by the addition of glycine, alanine or lysine to the compound of formula I.
Even more preferably the compound of general formula I is in the form of a pro-drug selected from the compounds of formulae:
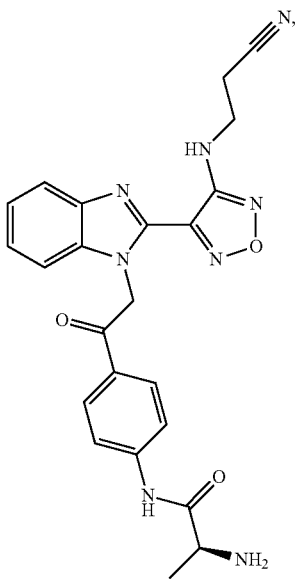
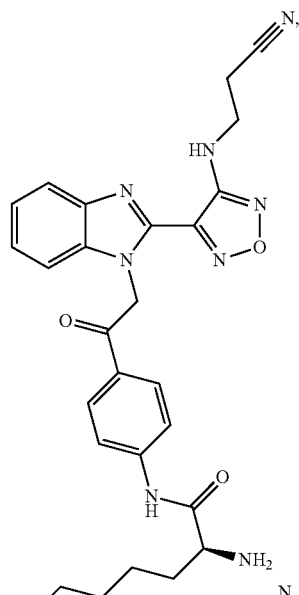
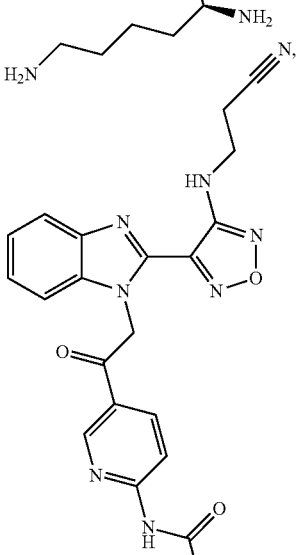
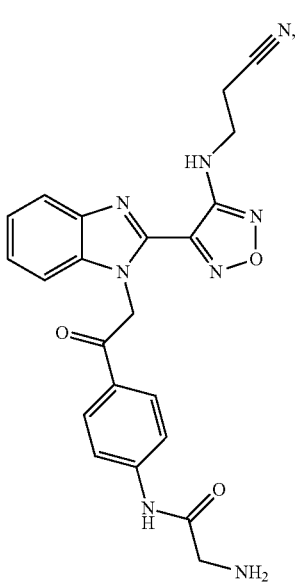

-continued

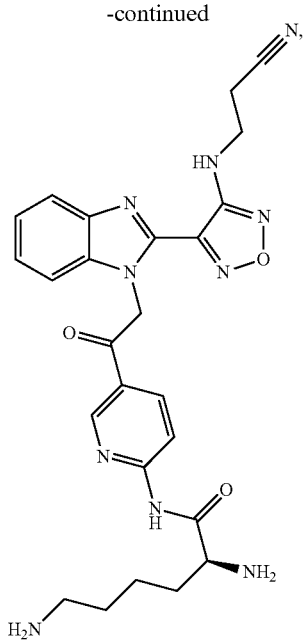

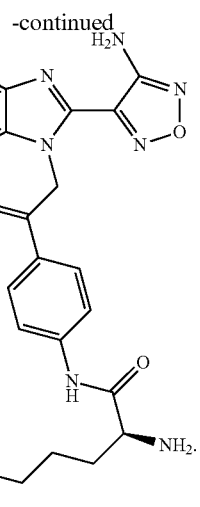

-continued

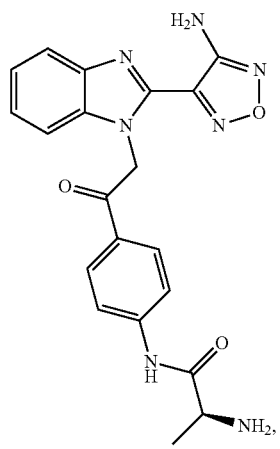

In an especially preferred embodiment the compound of general formula I is in the form of a pro-drug which has the following formula

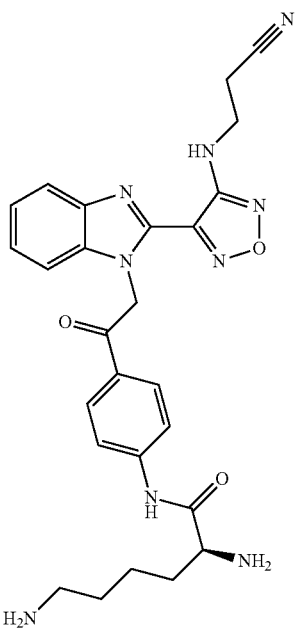

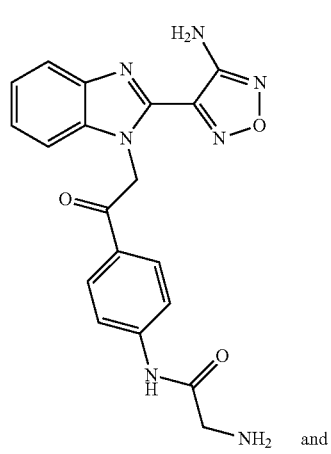

and

In a most especially preferred embodiment the compound according to the invention is a salt, preferably a hydrochloride salt, most preferably a dihydrochloride salt, of a compound of the following formula

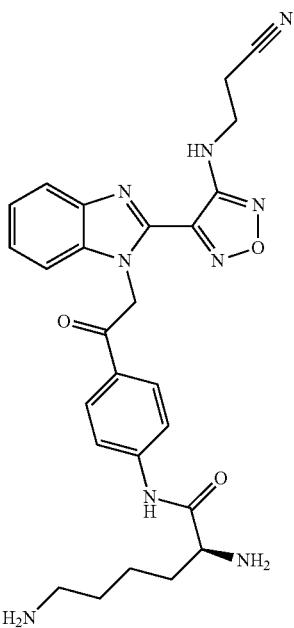

The pharmaceutically active metabolite in vivo in this case is BAL27862.

These pro-drugs may be prepared by processes that are known per se, in particular, a process, wherein a compound of formula (II)

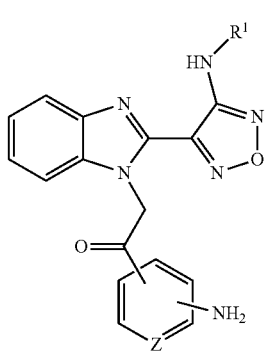

(II)

wherein $R^1$ is defined as for formula (I) and Z is CH or N, or a derivative of such a compound comprising functional groups in protected form,
or a salt thereof is
(1) acylated with an amino acid of formula (III)

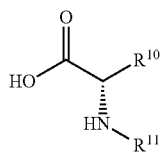

(III)

wherein
$R^{10}$ is selected from hydrogen (Gly); methyl (Ala) and protected aminobutyl (Lys) and
$R^{11}$ is a suitable amino protecting group, and (2) any protecting groups in a protected derivative of the resulting compound are removed to yield a pro-drug as shown above, and, if so desired,
(3) said pro-drug is converted into a salt by treatment with an acid, or a salt of a compound of formula (II) is converted into the corresponding free compound of formula (II) or into another salt, and/or a mixture of isomeric product compounds is separated into the individual isomers.

Acylation of a compound of formula (II) with an amino acid of formula (III) is performed in a manner known per se, usually in the presence of a suitable polar or dipolar aprotic solvent, with cooling or heating as required, for example in a temperature range from approximately minus 80° C. to approximately plus 150° C., more preferably from minus 30° C. to plus 120° C., especially in a range from approximately around 0° C. to the reflux temperature of the used solvent. Optionally a suitable base is added, in particularly an aromatic base like pyridine or collidine or a tertiary amine base such as triethylamine or diisopropylethylamine, or an inorganic basic salt, e.g. potassium or sodium carbonate.

Acylation may be accomplished under conditions used for amide formation known per se in peptide chemistry, e.g. with activating agents for the carboxy group, such as carbodiimides like N,N'-diethyl-, N,N'-dipropyl-, N,N'-diisopropyl-, N,N'-dicyclohexylcarbodiimide and N-(3-dimethylaminoisopropyl)-N'-ethylcarbodiimide-hydrochloride (EDC), or with agents such as 1-hydroxybenzotriazole (HOBt), benzotriazol-1-yloxytris(dimethylamino)-phosphonium hexafluorophosphate (BOP), O-(7-aza-benzotriazol-1-yl)-N,N,N',N'-tetramethyl-uronium hexafluorophosphate (HATU), 2-(2-oxo-1-(2H)-pyridyl)-1,1,3,3-tetramethyluronium tetrafluoroborate (TPTU), optionally in the presence of suitable bases, catalysts or co-reagents. The carboxy group may also be activated as acyl halogenide, preferably as acyl chloride, e.g. by reaction with thionylchloride or oxalylchloride, or as symmetrical or unsymmetrical anhydride, e.g. by reaction with halogeno formates like ethyl chloroformate, optionally in the presence of suitable bases, catalysts or co-reagents.

If one or more other functional groups, for example carboxy, hydroxy or amino, are or need to be protected in a compound of formula (II) or (III), because they should not take part in the reaction, these are such protecting groups as are usually applied in the synthesis of amides like, in particular peptide compounds, cephalosporins, penicillins, nucleic acid derivatives and sugars, which are known to the skilled persons. Suitable protecting groups for amino groups are for example t-butyl carbamate, benzyl carbamate or 9-fluorenylmethyl carbamate.

The protecting groups may already be present in precursors and should protect the functional groups concerned against unwanted secondary reactions, such as alkylations, acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, G. M. Wuts "Protective Groups in Organic Synthesis", Wiley, New York, 2006.

Disease

The compounds of general formula I according to the invention have been shown to arrest cell proliferation and induce cell death, for example by apoptosis.

Dysregulation of cell proliferation, or lack of appropriate cell death, has wide ranging clinical implications. A number of diseases associated with such dysregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like.

Cancer is associated with abnormal cell proliferation and cell death rates. As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or reestablished in epithelial cells, in endothelial cells, in muscle cells, and in others which have lost contact with extracellular matrix.

A compound according to general formula I or pharmaceutically acceptable derivatives thereof may be used for the prophylactic or especially therapeutic treatment of the human or animal body, in particular for treating a neoplastic disease, autoimmune disease, transplantation related pathology and/or degenerative disease. Examples of such neoplastic diseases include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non-Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

The compounds of general formula I or pharmaceutically acceptable derivatives thereof may be used to treat autoimmune diseases. Examples of such autoimmune diseases include, but are not limited to, systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis/polymyositis, autoimmune hemolytic anemia, thrompocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory diseases with a possibility of autoimmune pathogensesis, such as pyoderma gangrensosum, lichen ruber, sarcoidosis (including Lofgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, HenochSchoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-vu (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oropharynx, esophageus, stomach, small intestine, colon, and rectum, including parts of above mentioned organs down to single cell level and substructures, e.g. stem cells).

Particularly preferably, the disease according to the invention is a neoplastic or autoimmune disease. In an especially preferred embodiment the disease is cancer.

Examples of cancers in terms of the organs and parts of the body affected include, but are not limited to, the breast, cervix, ovaries, colon, rectum, (including colon and rectum i.e. colorectal cancer), lung, (including small cell lung cancer, non-small cell lung cancer, large cell lung cancer and mesothelioma), bone, endocrine system, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis. Preferably the cancer is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma, T-cell leukemia and sarcomas. More especially preferably the cancer is selected from the group consisting of breast cancer, cervical cancer, ovarian cancer, T-cell leukemia and lung cancer. In an especially preferred embodiment the cancer is selected from the group consisting of lung cancer, ovarian cancer and T-cell leukemia.

Samples

The measurement of the level of acetylated tubulin may be performed in vitro, on a sample of biological tissue derived from the subject. The sample may be any biological material separated from the body such as, for example, normal tissue, tumour tissue, cell lines, whole blood, serum, plasma, cerebrospinal fluid, lymph fluid, circulating tumour cells, cell lysate, tissue lysate, urine and aspirates. Preferably the sample is derived from normal tissue, tumour tissue, or circulating tumour cells. More preferably the sample is derived from tumour tissue or circulating tumour cells. In one particularly preferred embodiment the sample is derived from tumour tissue. For example, the level of acetylated tubulin may be measured in a fresh, frozen or formalin fixed/paraffin embedded tumour tissue sample.

The sample is pre-obtained from the subject before the sample is subjected to the method steps involving measuring the level of the biomarker. The methods for removal of the sample are well known in the art, and it may for example be removed from the subject by biopsy, for example by punch biopsy, core biopsy or aspiration fine needle biopsy, endoscopic biopsy, or surface biopsy. Blood may be collected by venipuncture and further processed according to standard techniques. Circulating tumour cells may also be obtained from blood based on, for example, size (e.g. ISET—Isolation by Size of Epithelial Tumour cells) or immunomagnetic cell enrichment. (e.g. Cellsearch®, Veridex, Raritan, N.J.).

Sample Comparison

The subject according to the invention may be human or animal. Preferably the subject is human.

The biomarker acetylated tubulin is measured ex vivo in a sample or samples taken from the human or animal body, preferably taken from the human body. The sample or samples are pre-obtained from the human or animal body, preferably pre-obtained from the human body before the sample is subjected to the method steps involving measuring the level of the biomarker.

A biomarker is in general a substance that is used as an indicator of a biological response, preferably as an indicator of the susceptibility to a given treatment, which in the present application is treatment with a compound of general formula I or a pharmaceutically acceptable derivative thereof.

In a particularly preferred embodiment, higher acetylated tubulin levels in the sample relative to a standard value or set of standard values predicts resistance.

As used herein, an increase or relatively high or high or higher levels relative to a standard level or set of standard levels means the amount or concentration of the biomarker in a sample is detectably greater in the sample relative to the standard level or set of standard levels. This encompasses at least an increase of, or higher level of, about 1% relative to the standard, preferably at least an increase of about 5% relative to the standard. More preferably it is an increase of, or higher level of, at least about 10% relative to the standard. More particularly preferably it is an increase of, or higher level of, at least about 20% relative to the standard. For example, such an increase of, or higher level of, may include, but is not limited to, at least about 1%, about 10%, about 20%, about 30%, about 50%, about 70%, about 80%, about 100%, about 150% or about 200% or more relative to the standard.

Preferably, higher acetylated tubulin levels in a sample or samples i) relative to a standard value or set of standard values from subjects with the same tumour histotype; or ii) taken after treatment initiation and compared to a sample or samples taken from the same subject before treatment initiation; or iii) relative to a standard value or set of standard values from normal cells or tissue;

are predictive of resistance.

More preferably, higher acetylated tubulin levels in a sample or samples i) relative to a standard value or set of standard values from subjects with the same tumour histotype; or ii) taken after treatment initiation and compared to a sample or samples taken from the same subject before treatment initiation;

are predictive of resistance.

Especially preferably, higher acetylated tubulin levels in a sample or samples taken after treatment initiation and compared to a sample or samples taken from the same subject before treatment initiation are predictive of resistance.

Also preferably, higher acetylated tubulin levels in a sample or samples relative to a standard value or set of standard values taken from subjects with the same tumour histotype are predictive of resistance.

In one preferred embodiment, for the case i) where the measurement is compared in a sample or samples relative to a standard value or set of standard values taken from samples from subjects with the same tumour histotype as the sample to which it is to be compared, the standard value or set of standard values are established from samples taken from a population of subjects with that cancer type. The samples from these standard subjects may for example be derived from the tumour tissue or blood, as long as the origin of the sample is consistent between the standard and the sample to be compared.

In another preferred embodiment, for the case ii) where the measurement is compared in a sample or samples taken after treatment initiation and compared to a sample or samples taken from the same subject before treatment initiation, it is measured preferably to predict acquired resistance. The samples are compared to cells or tissue from the same biological origin. The prediction of acquired resistance would then indicate that the treatment with the compound should be discontinued. The biomarker is thus used to monitor whether further treatment with the compound is likely to give the required response (e.g. reduction of abnormal cells), or whether the cells have become non-responsive or resistant to such treatment.

In yet another preferred embodiment, for the case iii) where the measurement is compared in a sample or samples relative to a standard value or set of standard values taken from normal cells or tissue, the standard value or set of standard values may be established from a sample of normal (e.g. non-tumorous) cells or tissue or body fluid. Such data may be gathered from a population of subjects in order to develop the standard value or set of standard values.

The standard value or set of standard values are established ex-vivo from pre-obtained samples which may be from cell lines,or preferably biological material taken from at least one subject and more preferably from an average of subjects (e.g., n=2 to 1000 or more). The standard value or set of standard values may then be correlated with the response data of the same cell lines, or same subjects, to treatment with a compound of general formula I or a pharmaceutically acceptable derivative thereof. From this correlation a comparator module, for example in the form of a relative scale or scoring system, optionally including cut-off or threshold values, can be established which indicates the levels of biomarker associated with a spectrum of response levels to the compound of formula I or a pharmaceutically acceptable derivative thereof. The spectrum of response levels may comprise relative sensitivity to the therapeutic activity of the compound, (e.g. high sensitivity to low sensitivity), as well as resistance to the therapeutic activity. In a preferred embodiment this comparator module comprises a cut-off value or set of values which predicts resistance to treatment.

For example, if an immunohistochemical method is used to measure the level of acetylated tubulin in a sample, standard values may be in the form of a scoring system. Such a system might take into account the percentage of cells in which staining for acetylated tubulin is present. The system may also take into account the relative intensity of staining in the individual cells. The standard values or set of standard values of the level of acetylated tubulin may then be correlated with data indicating the response, especially resistance, of the subject or tissue or cell line to the therapeutic activity of a compound of formula I or a pharmaceutically acceptable derivative thereof. Such data may then form part of a comparator module.

Response is the reaction of the cell lines, or preferably of the subject, or more preferably of the disease in a subject, to the therapeutic activity of a compound of general formula I or a pharmaceutically acceptable derivative thereof. The spectrum of response levels may comprise relative sensitivity to the therapeutic activity of the compound, (e.g. high sensitivity to low sensitivity), as well as resistance to the therapeutic activity. The response data may for example be monitored in terms of: objective response rates, time to disease progression, progression free survival, and overall survival.

The response of a cancerous disease may be evaluated by using criteria well known to a person in the field of cancer treatment, for example but not restricted to, Response Evaluation Criteria in Solid Tumors (RECIST) Guidelines, Source: Eisenhauer E A, Therasse P, Bogaerts J, Schwartz L H, Sargent D, Ford R, Dancey J, Arbuck S, Gwyther S, Mooney M, Rubinstein L, Shankar L, Dodd L, Kaplan R, Lacombe D, Verweij J. New response evaluation criteria in solid tumours: revised RECIST guideline (version 1.1). Eur J Cancer. 2009; 45:228-47;

RANO Criteria for High-Grade Gliomas, Source: Wen P Y, Macdonald D R, Reardon D A, Cloughesy T F, Sorensen A G, Galanis E, Degroot J, Wick W, Gilbert M R, Lassman A B, Tsien C, Mikkelsen T, Wong E T, Chamberlain M C, Stupp R, Lamborn K R, Vogelbaum M A, van den Bent M J, Chang S M. Updated response assessment criteria for high-grade gliomas: response assessment in neuro-oncology working group. J Clin Oncol. 2010,28 (11):1963-72;

CA-125 Rustin Criteria for Ovarian Cancer Response, Source: Rustin G J, Quinn M, Thigpen T, du Bois A, Pujade-Lauraine E, Jakobsen A, Eisenhauer E, Sagae S, Greven K, Vergote I, Cervantes A, Vermorken J. Re: New guidelines to evaluate the response to treatment in solid tumors (ovarian cancer). J Natl Cancer Inst. 2004; 96(6): 487-8;

and

PSA Working Group 2 Criteria for Prostate Cancer Response, Source: Scher H I, Halabi S, Tannock I, Morris M, Sternberg C N, Carducci M A, Eisenberger M A, Higano C, Bubley G J, Dreicer R, Petrylak D, Kantoff P, Basch E, Kelly W K, Figg W D, Small E J, Beer T M, Wilding G, Martin A, Hussain M; Prostate Cancer Clinical Trials Working Group. Design and end points of clinical trials for patients with progressive prostate cancer and castrate levels of testosterone: recommendations of the Prostate Cancer Clinical Trials Working Group. J Clin Oncol. 2008; 26(7):1148-59.

Resistance is associated with there not being an observable and/or measurable reduction in, or absence of, one or more of the following: reduction in the number of abnormal cells, preferably cancerous cells; or absence of the abnormal cells, preferably cancerous cells; for cancerous diseases: reduction in tumour size; inhibition (i.e., slowed to some extent and preferably stopped) of further tumour growth; reduction in the levels of tumour markers such as PSA and CA-125; inhibition (i.e., slowed to some extent and preferably stopped) of cancer cell infiltration into other organs (including the spread of cancer into soft tissue and bone); inhibition (i.e., slowed to some extent and preferably stopped) of tumour metastasis; alleviation of one or more of the symptoms associated with the specific cancer; and reduced morbidity and mortality.

In a preferred embodiment resistance means there is no observable and/or measurable reduction in, or absence of, one or more of the following criteria: reduction in tumour size; inhibition of further tumour growth, inhibition of cancer cell infiltration into other organs; and inhibition of tumour metastasis.

In a more preferred embodiment resistance refers to one or more of the following criteria: no reduction in tumour size; no inhibition of further tumour growth, no inhibition of cancer cell infiltration into other organs; and no inhibition of tumour metastasis.

Measurement of the aforementioned resistance criteria is according to clinical guidelines well known to a person in the field of cancer treatment, such as those listed above for measuring the response of a cancerous disease.

Response may also be established in vitro by assessing cell proliferation and/or cell death. For example, effects on cell death or proliferation may be assessed in vitro by one or more of the following well established assays: A) Nuclear staining with Hoechst 33342 dye providing information about nuclear morphology and DNA fragmentation which are hallmarks of apoptosis. B) Annexin V binding assay which reflects the phosphatidylserine content of the outer lipid bilayer of the plasma membrane. This event is considered an early hallmark of apoptosis. C) TUNEL assay (Terminal deoxynucleotidyl transferase mediated dUTP Nick End Labeling assay), a fluorescence method for evaluating cells undergoing apoptosis or necrosis by measuring DNA fragmentation by labeling the terminal end of nucleic acids. D) FACs analysis of fluorescently labeled cells (e.g.

GFP [green fluorescence protein]-expressing cells). Dying or dead cells show a decreased fluorescence signal in comparison to living cells, allowing the quantification of induction of cell death. E) MTS proliferation assay measuring the metabolic activity of cells. Viable cells are metabolically active whereas cells with a compromised respiratory chain show a reduced activity in this test. F) Crystal violet staining assay, where effects on cell number are monitored through direct staining of cellular components. G) Proliferation assay monitoring DNA synthesis through incorporation of bromodeoxyuridine (BrdU). Inhibitory effects on growth/proliferation can be directly determined. H) YO-PRO assay which involves a membrane impermeable, fluorescent, monomeric cyanine, nucleic acid stain, which permits analysis of dying (e.g. apoptotic) cells without interfering with cell viability. Overall effects on cell number can also be analysed after cell permeabilisation. I) Propidium iodide staining for cell cycle distribution which shows alterations in distribution among the different phases of the cell cycle. Cell cycle arresting points can be determined. J) Anchorage-independent growth assays, such as colony outgrowth assays which assess the ability of single cell suspensions to grow into colonies in soft agar.

In a preferred embodiment relating to determination of resistance in vitro, resistance means there is no decrease in the proliferation rate of abnormal cells and/or reduction in the number of abnormal cells. More preferably resistance means there is no decrease in the proliferation rate of cancerous cells and/or no reduction in the number of cancerous cells. The reduction in the number of abnormal, preferably cancerous, cells may occur through a variety of programmed and non-programmed cell death mechanisms. Apoptosis, caspase-independent programmed cell death and autophagic cell death are examples of programmed cell death. However the cell death criteria involved in embodiments of the invention are not to be taken as limited to any one cell death mechanism.

Acetylated Tubulin

Preferred examples of the protein sequence of alpha and beta tubulin (human alpha and beta tubulin) are listed in SEQ. ID No. 1-6, FIGS. 9-14. Alpha or beta tubulin, especially alpha tubulin, is a precursor of acetylated tubulin. As described previously, a specific lysine residue in the tubulin chain may be acetylated or deacetylated. The term acetylated tubulin also encompasses homologues, mutant forms, allelic variants, isoforms, splice variants and equivalents of the sequences represented by SEQ ID NO 1-6, with the proviso that a lysine residue in the sequence is acetylated. More preferably it encompasses sequences having at least about 75% identity, especially preferably at least about 85% identity, particularly preferably at least about 95% identity, and more particularly preferably about 99% identity to said sequences, with in each case the proviso that a lysine residue in the sequence is acetylated. Particularly preferably lysine 40 of alpha tubulin is acetylated.

Level of Acetylated Tubulin

The level of acetylated tubulin may be assayed in the sample by protein analysis techniques well known to a skilled person. Examples of methods known in the art which are suitable to measure the level of acetylated tubulin at the protein level include, but are not limited to, i) immunohistochemistry (IHC) analysis, ii) western blotting iii) immunoprecipitation iv) enzyme linked immunosorbant assay (ELISA) v) radioimmunoassay vi) Fluorescence activated cell sorting (FACS) vii) mass spectrometry, including matrix assisted laser desorption/ionisation (MALDI, e.g. MALDI-TOF) and electrospray ionisation mass-spectrometry (ESI-MS).

The antibodies involved in some of the above methods may be monoclonal or polyclonal antibodies, antibody fragments, and/or various types of synthetic antibodies, including chimeric antibodies. The antibody may be labeled to enable it to be detected or capable of detection following reaction with one or more further species, for example using a secondary antibody that is labeled or capable of producing a detectable result. Antibodies specific to the acetylated alpha tubulin are available commercially from Sigma. Additionally antibodies to acetylated alpha tubulin and acetylated beta tubulin can be prepared via conventional antibody generation methods well known to a skilled person.

Preferred methods of protein analysis are ELISA, mass spectrometry techniques, immunohistochemistry and western blotting, more preferably western blotting and immunohistochemistry. In western blotting, also known as immunoblotting, labelled antibodies may be used to assess levels of protein, where the intensity of the signal from the detectable label corresponds to the amount of protein, and can be quantified for example by densitometry.

Immunohistochemistry again uses labelled antibodies to detect the presence and relative amount of the biomarker. It can be used to assess the percentage of cells for which the biomarker is present. It can also be used to assess the localisation or relative amount of the biomarker in individual cells, the latter is seen as a function of the intensity of staining.

ELISA stands for enzyme linked immunosorbant assay, since it uses an enzyme linked to an antibody or antigen for the detection of a specific protein. ELISA is typically performed as follows (although other variations in methodology exist): a solid substrate such as a 96 well plate is coated with a primary antibody, which recognises the biomarker. The bound biomarker is then recognised by a secondary antibody specific for the biomarker. This may be directly joined to an enzyme or a third anti-immunoglobulin antibody may be used which is joined to an enzyme. A substrate is added and the enzyme catalyses a reaction, yielding a specific colour. By measuring the optical density of this colour, the presence and amount of the biomarker can be determined.

Uses of Biomarker

The biomarker may be used to predict acquired resistance of the disease in a subject to the compound of general formula I or a pharmaceutically acceptable derivative thereof as defined above.

The biomarker may be used to select subjects suffering or predisposed to suffering from a disease, preferably cancer, for treatment with a compound of general formula I or a pharmaceutically acceptable derivative thereof as defined above. The levels of such a biomarker may be used to identify subjects likely to respond or to not respond or to continue to respond or to not continue to respond to treatment with such agents. Preferably the levels of such a biomarker may be used to identify subjects likely to continue to respond or to not continue to respond to treatment with such agents. Stratification of subjects may be made in order to avoid unnecessary treatment regimes. In particular the biomarker may be used to identify subjects from whom a sample or samples do not display a higher level of acetylated tubulin, relative to a standard level or set of standard levels, whereupon such subjects may then be selected for treatment with the compound of formula I or a pharmaceutically acceptable derivative thereof as defined above. More particularly the biomarker may be used to identify subjects from whom a sample or samples do not display a higher level of acetylated tubulin, relative to a level measured before treatment initiation, whereupon such subjects may then be selected for continued treatment with the compound of formula I or a pharmaceutically acceptable derivative thereof as defined above.

The biomarker may also be used to assist in the determination of treatment regimes, regarding amounts and schedules of dosing. Additionally, the biomarker may be used to assist in the selection of a combination of drugs to be given to a subject, including a compound or compounds of general formula I or a pharmaceutically acceptable derivative thereof, and another chemotherapeutic (cytotoxic) agent or agents. Furthermore, the biomarker may be used to assist in the determination of therapy strategies in a subject including whether a compound of general formula I or a pharmaceutically acceptable derivative thereof is to be administered in combination with targeted therapy, endocrine therapy, radiotherapy, immunotherapy or surgical intervention, or a combination of these.

Acetylated tubulin may also be used in combination with other biomarkers to predict the response to a compound of general formula I or a pharmaceutically acceptable derivative thereof and to determine treatment regimes. It may furthermore be used in combination with chemo-sensitivity testing to predict resistance and to determine treatment regimes. Chemo-sensitivity testing involves directly applying a compound of general formula I to cells taken from the subject, for example from a subject with haematological malignancies or accessible solid tumours, for example breast, head and neck cancers or melanomas, to determine the response of the cells to the compound.

Method of Treatment

The invention also involves in some aspects a method of treatment and acetylated tubulin for use in a method of treatment, wherein the level of acetylated tubulin is first established relative to a standard level or set of standard levels or pre-treatment initiation levels and then a compound of general formula I or a pharmaceutically acceptable derivative thereof as defined above, is administered if the level of acetylated tubulin in said sample is not higher than standard value or set of standard values or has not increased relative to pre-treatment initiation levels respectively. The compound of formula I or a pharmaceutically acceptable derivative thereof may be administered in a pharmaceutical composition, as is well known to a person skilled in the art. Suitable compositions and dosages are for example disclosed in WO 2004/103994 A1 pages 35-39, which are specifically incorporated by reference herein. Compositions for enteral administration, such as nasal, buccal, rectal or, especially, oral administration, and for parenteral administration, such as intravenous, intramuscular or subcutaneous administration, to warm-blooded animals, especially humans, are especially preferred. More particularly, compositions for intravenous administration are preferred.

The compositions comprise the active ingredient and a pharmaceutically acceptable carrier. An example of a composition includes, but is not limited to, the following: 5000 soft gelatin capsules, each comprising as active ingredient 0.05 g of one of the compounds of general formula (I), are prepared as follows: 250 g pulverized active ingredient is suspended in 2 liter Lauroglykol® (propylene glycol laurate, Gattefossé S. A., Saint Priest, France) and ground in a wet pulverizer to produce a particle size of about 1 to 3 µm. 0.419 g portions of the mixture are then introduced into soft gelatin capsules using a capsule-filling machine.

The invention also relates in one aspect to a method of treating a neoplastic or autoimmune disease, preferably cancer, by first decreasing the level of acetylated tubulin in a subject that has a sample with a higher level of acetylated tubulin compared to a standard level or set of standard levels or pre-treatment initiation levels, and then treating the subject with a compound of general formula I or a pharmaceutically acceptable derivative as defined above. The level of acetylated tubulin may be decreased by direct or indirect chemical or genetic means. Examples of such methods are treatment with a drug that results in reduced acetylated tubulin expression, targeted delivery of viral, plasmid or peptide constructs, or antibody or siRNA or antisense to downregulate the level of acetylated tubulin. For example siRNA may be used to reduce the level of alphaTAT1 or delivery of a plasmid may be used to increase the expression of SirT2, and thereby reduce the level of acetylated tubulin in the cell. The subject may then be treated with a compound of general formula I or a pharmaceutically acceptable derivative thereof.

A compound of general formula I or a pharmaceutically acceptable derivative thereof can be administered alone or in combination with one or more other therapeutic agents. Possible combination therapy may take the form of fixed combinations, or the administration of a compound of the invention and one or more other therapeutic agents which are staggered or given independently of one another, or the combined administration of fixed combinations and one or more other therapeutic agents. A compound of general formula I or a pharmaceutically acceptable derivative thereof can, besides or in addition, be administered especially for tumour therapy in combination with chemotherapy (cytotoxic therapy), targeted therapy, endocrine therapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemo-preventive therapy, for example in patients at risk.

Kit and Device

In one aspect the invention relates to a kit and in another aspect to a device for predicting the response, preferably of a disease in a subject, to a compound of general formula I or a pharmaceutically acceptable derivative thereof as defined above, comprising reagents necessary for measuring the level of acetylated tubulin in a sample. Preferably, the reagents comprise a capture reagent comprising a detector for acetylated tubulin and a detector reagent.

The kit and device may also preferably comprise a comparator module which comprises a standard value or set of standard values to which the level of acetylated tubulin in the sample is compared. In a preferred embodiment, the comparator module is included in instructions for use of the kit. In another preferred embodiment the comparator module is in the form of a display device, for example a strip of colour or numerically coded material which is designed to be placed next to the readout of the sample measurement to indicate resistance levels. The standard value or set of standard values may be determined as described above.

The reagents are preferably antibodies or antibody fragments which selectively bind to acetylated tubulin. These may for example be in the form of one specific primary antibody which binds to acetylated tubulin and a secondary antibody which binds to the primary antibody, and which is itself labelled for detection. Alternatively, the primary antibody may also be labelled for direct detection. The kits or devices may optionally also contain a wash solution(s) that selectively allows retention of the bound biomarker to the capture reagent as compared with other biomarkers after washing. Such kits can then be used in ELISA, western blotting, flow cytometry, immunohistochemistry or other immunochemical methods to detect the level of the biomarker.

More preferably the kit comprises a compound of general formula I, or a pharmaceutically acceptable derivative thereof as defined above. This compound may then be administered to the subject, in accordance with the level of the biomarker in the sample from the subject, as measured by the reagents comprised in the kit. Therefore the kit according to the invention may be used in the method of treatment according to the invention, as defined above. In an especially preferred embodiment the kit comprises a compound of the following formula or a pharmaceutically acceptable salt thereof.

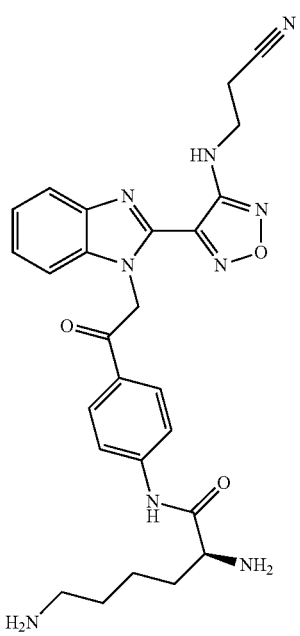 [SMILES: N#CCCNc1nonc1-c1nc2ccccc2n1CC(=O)c1ccc(NC(=O)[C@@H](N)CCCCN)cc1]

In a particularly preferred embodiment of the kit the pharmaceutically acceptable salt is a dihydrochloride salt. In another aspect the invention relates to the use of such a kit as described above.

Furthermore the device may comprise imaging devices or measurement devices (for example, but not restricted to, measurement of fluorescence) which further process the measured signals and transfer them into a scale in a comparator module.

In the present specification the words "comprise" or "comprises" or "comprising" are to be understood as to imply the inclusion of a stated item or group of items, but not the exclusion of any other item or group of items.

Experimental Methodology

Immunofluorescent Staining of Cultured Cells

A549 human non-small cell lung cancer (NSCLC, ATCC reference number CCL-185) cells, HeLa cervical cancer cells (ATCC reference number CCL-2) and SKBR3 breast carcinoma cells (ATCC reference number HTB-30) were seeded at densities of 50% on round microscope coverslips and cultured for 24 hours in RPMI-1640 containing 10% FCS (also referred to as FBS) at 37° C., 5% $CO_2$. Compounds to be tested were dissolved in DMSO. The cell culture medium was replaced with medium containing the diluted compound(s) (paclitaxel, vinblastine, colchicine, nocodazole were purchased from Sigma-Aldrich) or vehicle. After treatment for the times indicated in the Brief Description of the Figures, coverslips were washed and cells were fixed in methanol/acetone (1:1) for 5 minutes at room temperature and subsequently incubated in blocking buffer (0.5% BSA and 0.1% TX-100 in PBS) for 30 minutes at room temperature. Specimens were then incubated with anti-alpha tubulin antibody (Sigma, 1:2000) for 1 hour at room temperature in blocking buffer. After several washing steps cells were incubated with AlexaFluor-488 goat-anti-mouse IgG (Molecular Probes, 1:3000) for 1 hour at room temperature followed by several washing steps with blocking buffer. Specimens were then mounted with ProLong Gold antifade (Molecular Probes) sealed with nail polish and examined with a Leica immunofluorescence microscope. Images were captured with a cooled CCD-camera and processed by ImageJ software.

Generation and Crystal Violet or Cell Death Assay of BAL27862-Resistant Cell Lines BAL27862-resistant sublines of human non-small cell lung cancer (H460 ATCC reference HTB-177; A549 ATCC reference CCL-185), ovarian cancer (SKOV3 ATCC reference HTB-77) and T-cell leukemia (Jurkat ATCC reference TIB-152) cell lines were generated by long-term selection in complete cell culture medium (RPMI-1640 containing 10% FBS; Sigma-Aldrich) by increasing BAL27862 concentrations in a stepwise fashion. Dependent on the cell line, the selection process was carried out for 8-12 months in order to achieve resistance factors (ratio of $IC_{50}$ or $EC_{50}$ of resistant cell line versus the $IC_{50}$ or $EC_{50}$ of the appropriate parental cell line) between 3 and 22.5. The resistance factors were determined for the adherent cell lines H460, A549 and SKOV3 by measuring proliferation using the Crystal Violet assay, whereas for the suspension Jurkat cell line cell death was measured using FACS. The resistant sub lines were expanded at the highest tolerated BAL27862 concentration and subsequently frozen and stored in liquid nitrogen.

A549 (2000 cells/well), H460 (1000 cells/well) and SKOV3 (2000 cells/well) cells were seeded in 96 well plates. After 24 hours incubation, the cells were incubated for 72 hours with DMSO, BAL27862, colchicine, nocodazole, paclitaxel or vinblastine diluted in complete medium (final concentration DMSO max. 0.5%). After medium was removed, cells were fixed and stained by adding 50 µl Crystal Violet stain (0.2% Crystal Violet in 50% Methanol) per well. Plates were incubated for 1 hour at room temperature. Subsequently the stain was decanted and plates were washed 4 times with double-distilled water. Plates were air-dried for several hours. Stain was dissolved by adding 100 µl buffer (0.1 M Tris pH 7.5, 0.2% SDS, 20% Ethanol) per well and shaking the plates. Absorbance at 590 nm was measured using a SpectraMax M2e plate reader (Molecular Devices).

Jurkat cells stably expressing GFP (green fluorescence protein) were incubated with increasing BAL27862 concentrations in culture medium for 72 hours and then analyzed by FACS (excitation at 488 nM, emission at 525 nM). Dying or dead cells, showing a decreased fluorescence activity in comparison to living cells, were quantified (*Green fluorescent protein as a novel tool to measure apoptosis and necrosis*. Strebel et al, 2001, Cytometry 43(2): 126-133).

Antiproliferative $IC_{50}$ and cell death $EC_{50}$ values were calculated from concentration response curves using Graph-Pad Prism software. Resistance factors were calculated as a ratio of the $IC_{50}$ or $EC_{50}$ in the resistant line variant versus the $IC_{50}$ or $EC_{50}$ in the parental line.

Protein Analysis

Cells were washed with ice-cold PBS containing 1 mM phenylmethylsulfonyl fluoride (PMSF) and with ice-cold buffer containing 50 mM HEPES (pH 7.5), 150 mM NaCl, 25 mM β-glycerophosphate, 25 mM NaF, 5 mM EGTA, 1 mM EDTA, 15 mM pyrophosphate, 2 mM sodium orthovanadate, 10 mM sodium molybdate, leupeptin (10 μg/mL), aprotinin (10 μg/mL) and 1 mM PMSF. Cells were extracted in the same buffer containing 1% NP40. After homogenization, lysates were clarified by centrifugation and frozen at −80° C.

Protein concentration was determined with the BCA Protein Assay (Pierce). Immunoblotting was performed using 20 μg of total protein per lane. Protein was separated on a 10% SDS-gel and transferred to a PVDF membrane using Semidry Blotting (90 min, 50 mA/gel). Tubulin acetylation was measured using a mouse monoclonal anti-acetylated tubulin antibody (Sigma, reference number T7451): 1:10'000 dilution in PBS 5% milk/0.1% Tween. The actin antibody used was a mouse monoclonal (Chemicon, reference number MAB1501): 1:5'000 dilution in PBS 5% milk/0.1% Tween. The secondary antibody used for immunoblotting was peroxidase-conjugated goat anti-mouse (Jackson ImmunoResearch Laboratories INC: #115-035-146 JIR), used at a dilution of 1:5'000 in PBS plus 0.5% milk and 0.1% Tween. Labelled bands were revealed using a Raytest Stella 3200 High Performance Imaging System.

DETAILED EXAMPLES

Example 1

A Distinct Mitotic Phenotype Induced by Compounds of General Formula I

Figure 2:
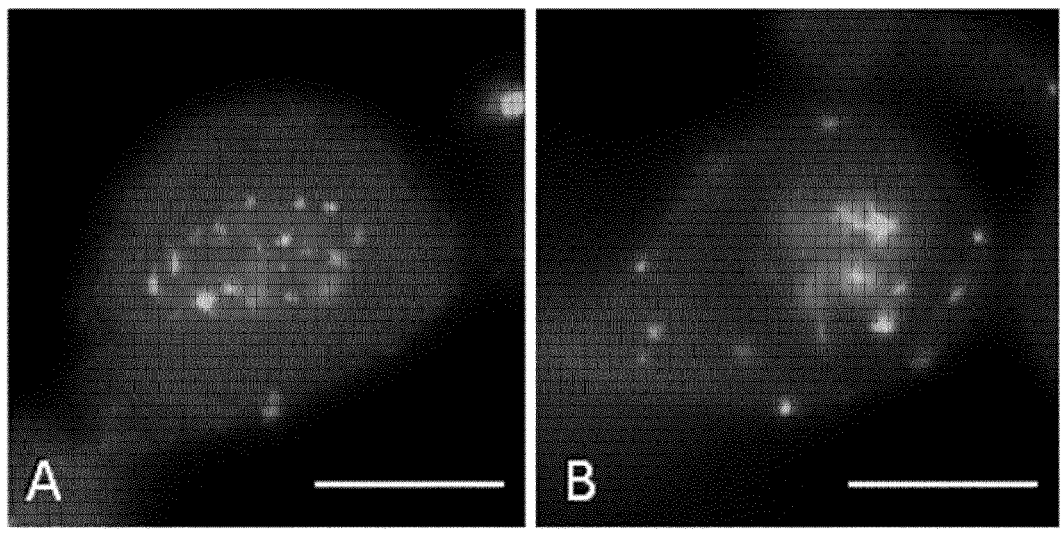
FIG. 2: Shows the treatment of A549 NSCLC cells with the Compounds B and C. The microtubules of mitotic or G2/M arrested A549 NSCLC cells were stained after 24 hours treatment with 80 nM or 20 nM of Compounds B and C, respectively. The white scale bar represents 10 micrometers.
Figure 3:
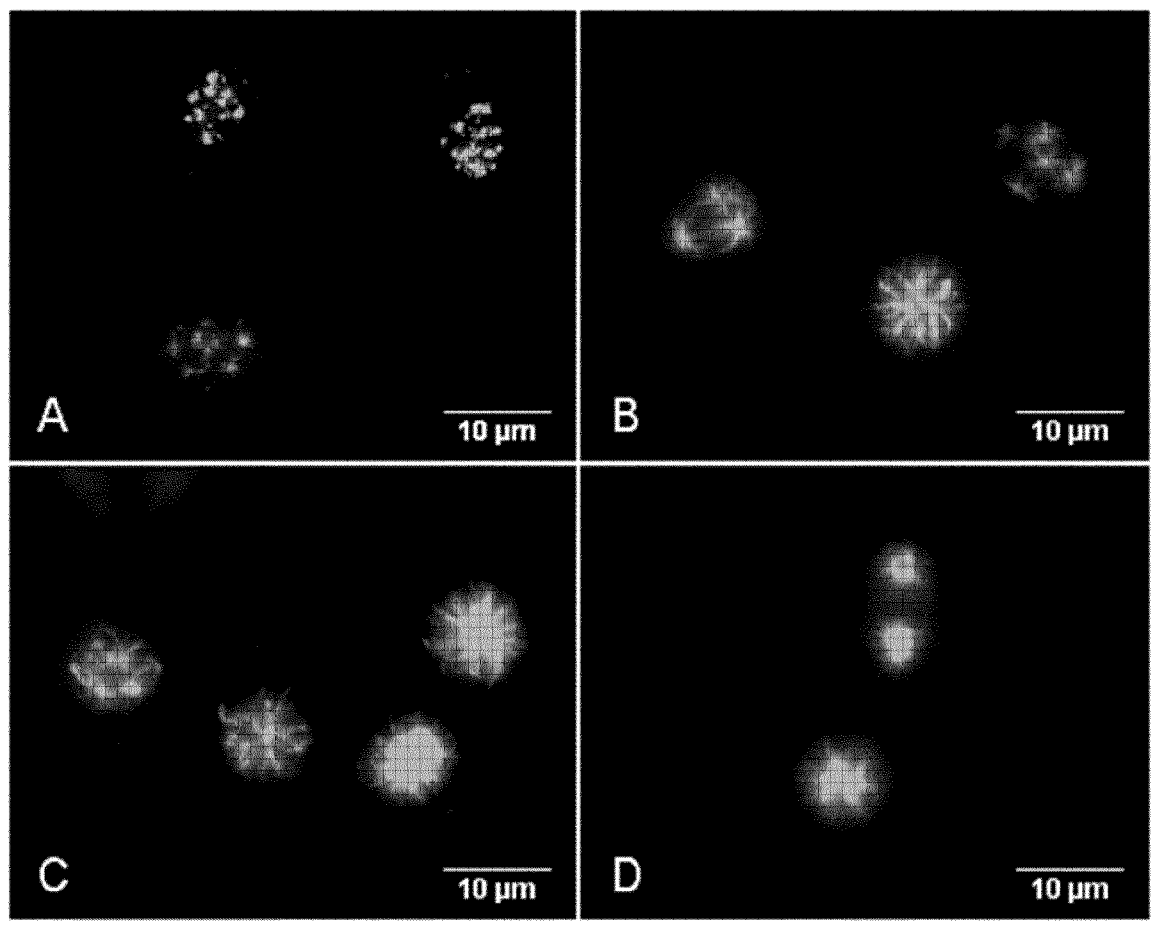
FIG. 3: Shows a comparison of treatment of cells with BAL27862 compared to conventional microtubule targeting agents. Microtubules of mitotic or G2/M arrested A549 NSCLC cells were stained after 24 hours of treatment with 50 nM of A: BAL27862; B: vinblastine; C: colchicine; D: paclitaxel. Stacks of images taken every 1 μm were processed by using ImageJ software.
Figure 4:
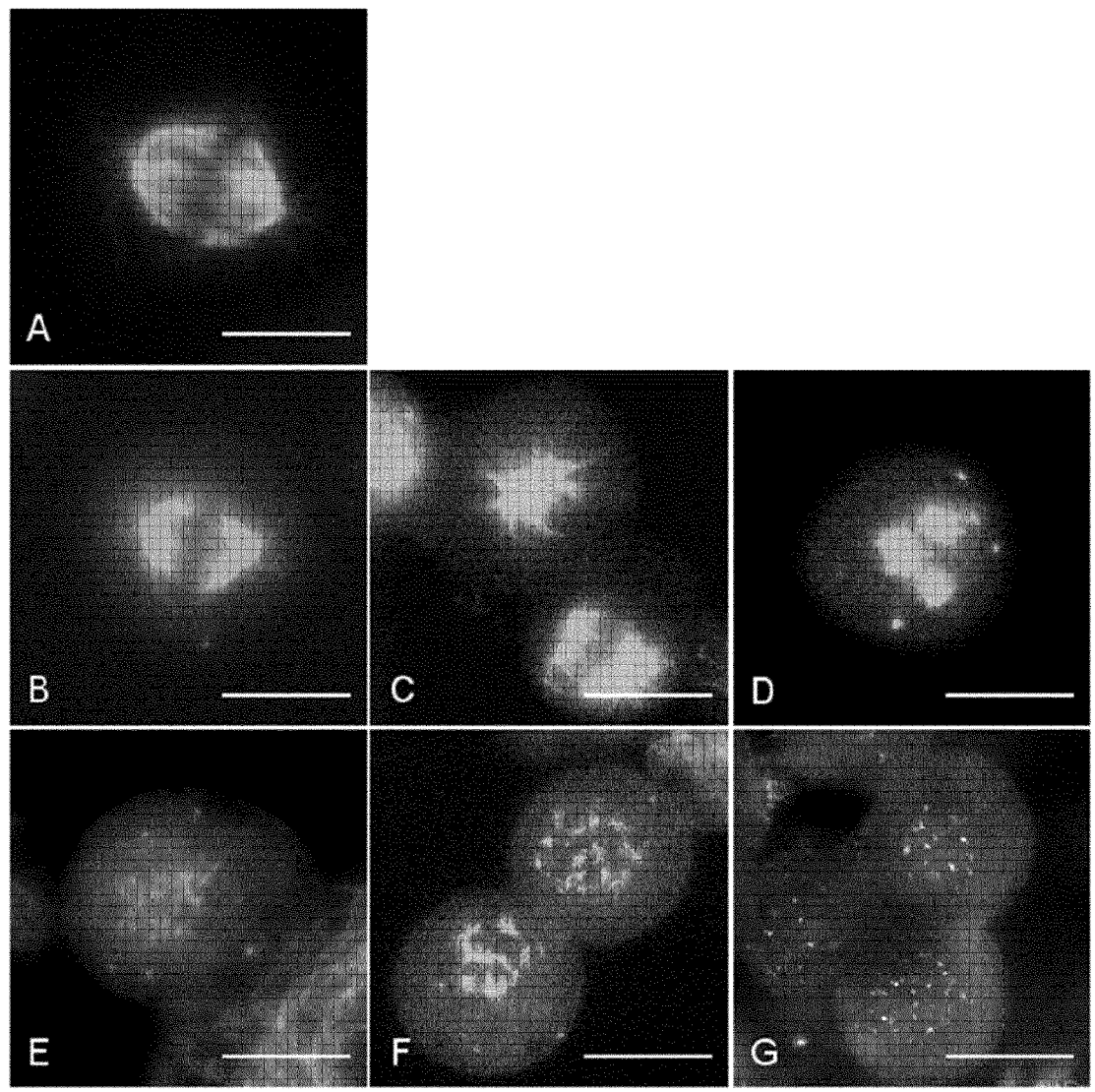
FIG. 4: Shows a comparison of treatment of A549 NSCLC cells with BAL27862 compared to nocodazole. Microtubules of mitotic or G2/M arrested cells were stained after 24 h of treatment with various concentrations of nocodazole (B, C & D) and BAL27862 (E, F & G). A: control, B: Nocodazole 50 nM, C: Nocodazole 100 nM, D: Nocodazole 200 nM, E: BAL27862 20 nM; F: BAL27862 30 nM and G: BAL27862 50 nM. The white scale bar represents 10 micrometers. Representative images of the microtubule phenotypes observed are shown.

Treatment with compound A (BAL27862) or with compound B or compound C, induced a highly reproducible and distinct microtubule phenotype in all tumour cell lines tested (shown for compound A in A549, HeLa and SKBR3 cells in FIG. 1, and for compound B and compound C in A549 cells in FIG. 2). In dividing cells an apparent fragmentation of the mitotic spindle occurred, resulting in the formation of dot-like structures (FIG. 1). This phenotype was shown to be distinct from that observed with conventional microtubule targeting agents, such as the microtubule stabiliser paclitaxel and the microtubule destabilisers vinblastine and colchicine (FIG. 3) and nocodazole (FIG. 4).

Example 2

Figure 5:
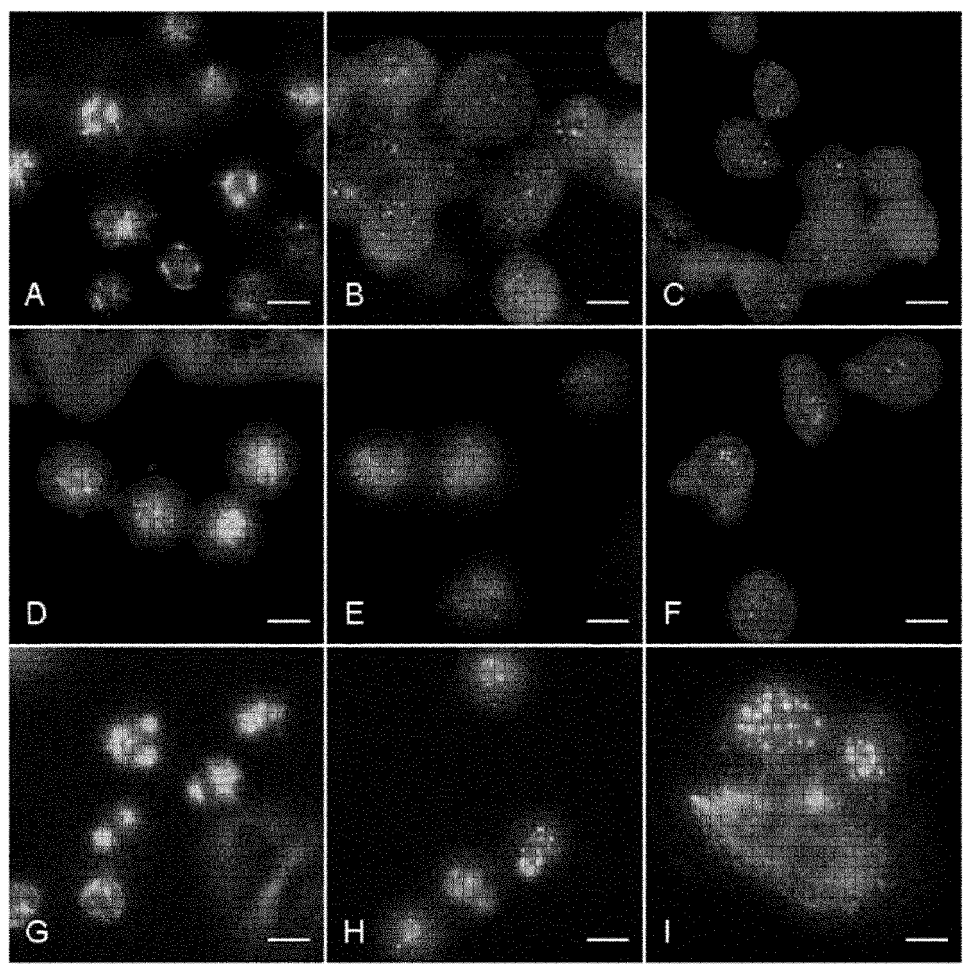
FIG. 5: Shows a combination of treatment with BAL27862 and conventional microtubule-targeting agents. Microtubules of mitotic or G2/M arrested A549 NSCLC cells were stained after treatment for the times indicated below. 50 nM BAL27862, 50 nM vinblastine, 50 nM colchicine and 25 nM paclitaxel were used. The white scale bar represents 10 micrometers.
Figure 6:
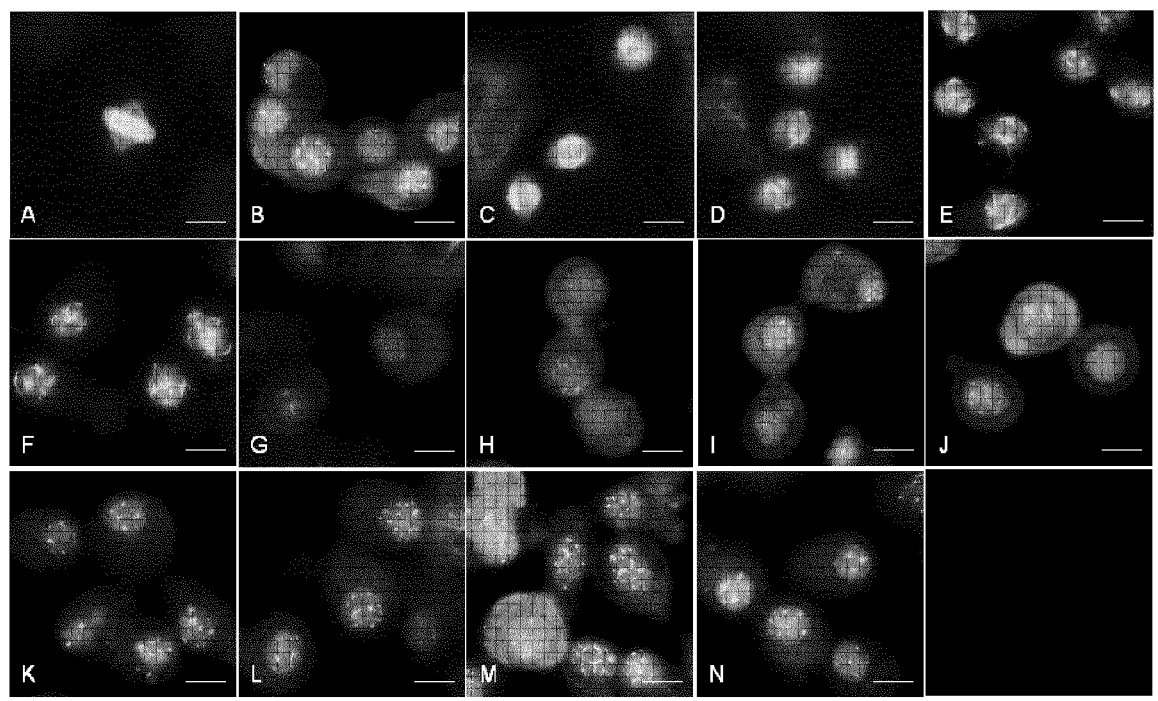
FIG. 6: Shows a combination of treatment with BAL27862 and nocodazole. Microtubules of mitotic or G2/M arrested A549 NSCLC cells were stained after treatment for the times indicated below. 25 nM BAL27862 and nocodazole at the concentrations indicated below were used. The white scale bar represents 10 micrometers.

BAL27862 Overcomes Microtubule Phenotype Induced by Conventional Microtubule-Targeting Drugs in a Dominant Fashion In order to show the uniqueness of its activity on microtubules, BAL27862 was tested in combination with vinblastine, colchicine and paclitaxel (FIG. 5) and nocodazole (FIG. 6) using A549 cells. Treatment with vinblastine, colchicine, paclitaxel or nocodazole alone induced the mitotic microtubule phenotypes characteristic of these agents. However, combination treatment with BAL27862 for the last 4 hours resulted in disruption of the microtubule structures; creating a phenotype consistent with treatment of BAL27862 alone, despite the continued presence of vinblastine, colchicine, paclitaxel or nocodazole. In contrast, treating first with BAL27862 and subsequently for 4 hours in combination with vinblastine, colchicine, paclitaxel or nocodazole had no impact on the observed microtubule phenotype that was consistent with treatment with BAL27862.

These data demonstrate that compounds of formula I affect microtubule biology consistently, but in a different manner than conventional microtubule targeting agents.

Detailed Examples According to the Invention

Example 3

Increased Acetylated Tubulin Expression is Observed in Tumour Lines Selected for Resistance to a Compound of General Formula I In vitro selection for resistance to BAL27862 resulted in the generation of 4 relatively resistant tumour cell lines, with the following resistance factors versus parental lines (based on $IC_{50}$ [A549, SKOV3, H460] or $EC_{50}$ [Jurkat] determinations using the Crystal Violet or FACs cell death assay, respectively): A549 (3.0 fold); SKOV3 resistant 1 (7.6 fold); SKOV3 resistant 2 (11.6 fold); H460 (5.3 fold); Jurkat (22.5 Fold) (Table 1).

TABLE 1

| Treatment compound | Resistance factors (ratio $IC_{50}$ or $EC_{50}$ BAL27862-resistant cell line variant versus $IC_{50}$ or $EC_{50}$ parental cell line) | | | | |
|---|---|---|---|---|---|
| | A549 | H460 | SKOV3 resistant 1 | SKOV3 resistant 2 | Jurkat |
| BAL27862 | 3.0 | 5.3 | 7.6 | 11.6 | 22.5 |
| Colchicine | 0.9 | 1.6 | 2.0 | 2.8 | nd |
| Nocodazole | 1.6 | 1.3 | 3.6 | 3.9 | nd |
| Vinblastine | 2.3 | 4.6 | 15.7 | 17.8 | nd |
| Paclitaxel | 0.06 | 0.3 | 0.4 | 0.5 | nd | nd: not determined

In general these BAL27862-resistant cells exhibited a different level of response to other microtubule destabilising agents, such as colchicine, nocodazole and vinblastine, as compared to BAL27862; and indeed increased sensitivity to the microtubule stabiliser paclitaxel was observed in all lines tested (Table 1).

Figure 7:
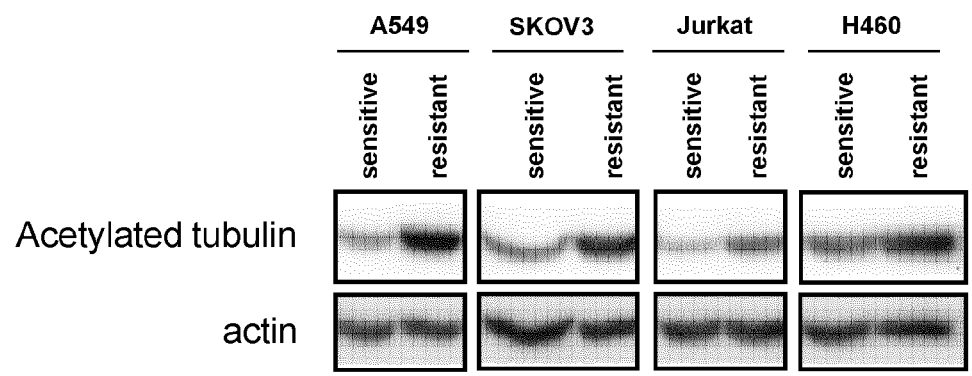
FIG. 7: Shows tumour cell lines which were selected for resistance to BAL27862 through in vitro cultivation in the presence of the compound. Based on $IC_{50}$ (for proliferation: A549, SKOV3, H460) or $EC_{50}$ (for cell death: Jurkat) determinations, BAL27862 resistance factors versus parental lines were: A549 (3.0 fold); SKOV3 (7.6 fold-resistant 1 line); Jurkat (22.5 fold), H460 (5.3 fold) (see Table 1). Whole cell protein extracts were prepared from parental and resistant lines and analysed by immunoblotting for acetylated tubulin expression. Actin levels were included as a loading control.
Figure 8:
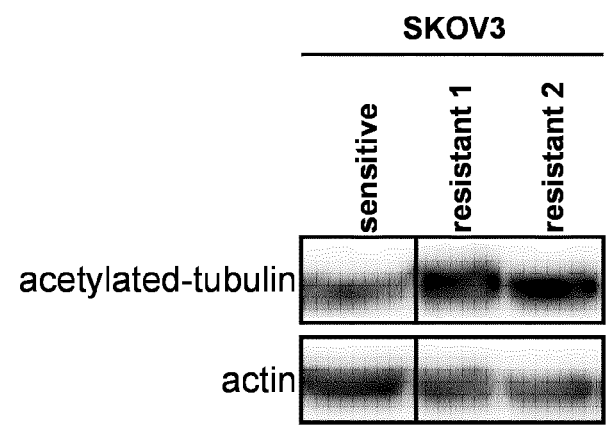
FIG. 8: Shows that increased acetylated tubulin protein levels are maintained in SKOV3 tumour lines during resistance development. SKOV3 tumour cell lines were selected for resistance to BAL27862 through in vitro cultivation in the presence of BAL27862 for increasing time periods. Based on $IC_{50}$ determinations, BAL27862 resistance factors versus parental lines were: SKOV3 resistant 1 (7.6 fold), SKOV3 resistant 2 (11.6 fold) (see Table 1). Whole cell protein extracts were prepared from parental and resistant lines and analysed by immunoblotting for acetylated tubulin expression. Actin levels act as a loading control.

Extraction and immunoblot analysis of these lines to measure the acetylated tubulin levels, followed by comparison to BAL27862 resistance data (Table 1), showed that acetylated tubulin is higher in the resistant lines, as compared to the parental lines (FIG. 7). This was maintained throughout resistance development in the SKOV3 cells (FIG. 8). These data show the association of increased acetylated tubulin expression levels with acquired resistance to BAL27862.

LIST OF ABBREVIATIONS

A549 human non-small cell lung cancer cell line
alphaTAT1 alpha-tubulin N-acetyltransferase 1
BCA bicinchoninic acid
BrdU bromodeoxyuridine
BSA bovine serum albumin
CA-125 cancer antigen 125
CCD charge-coupled device
cDNA complementary deoxyribonucleic acid
CREST limited scleroderma syndrome
DMSO dimethylsulphoxide DNA deoxyribonucleic acid
dUTP 2'-Deoxyuridine 5'-Triphosphate
EDTA Ethylenediaminetetraacetic acid
EGTA Ethyleneglycol-bis(β-aminoethyl)-N,N,N',N'-tetraacetic acid
ELISA enzyme-linked immunosorbent assay
Elp3 elongator complex protein 3
ESI-MS electrospray ionisation mass-spectrometry
FACS fluorescence activated cell scan/sorting
FCS/FBS foetal calf/foetal bovine serum
G2/M transition from G2 to the mitotic phase in the cell cycle
GFP green fluorescence protein
HDAC6 histone deacetylase 6
HeLa human squamous cell cancer cell line
HEPES 4-(2-Hydroxyethyl)piperazine-1-ethanesulphonic acid
IHC Immunohistochemistry
ISET Isolation by size of epithelial tumor cells
Jurkat human T-cell leukemia cell line
MAB monoclonal antibody
MALDI matrix-assisted-laser-desorption/ionisation mass-spectrometry
MALDI-TOF matrix-assisted-laser-desorption/ionisation-time-of-flight-mass-spectrometry
MDRI multi-drug resistant protein
mRNA messenger ribonucleic acid
MTS 3-(4,5-dimethylthiazol-2-yl)-5-(3-carboxymethoxyphenyl)-2-(4-sulphophenyl)-2H-tetrazolium
NCBI National center for Biotechnology Information
NSCLC non-small cell lung cancer
NP40 Nonidet P40
PBS phosphate buffered saline
P-gp P-glycoprotein
PMSF phenylmethylsulphonyl fluoride
PSA prostate-specific antigen
PVDF polyvinylidene fluoride
RANO response assessment for high-grade gliomas
RECIST response evaluation criteria in solid tumors
RPMI-1640 cell culture medium used for culturing transformed and non-transformed eukaryotic cells and cell lines
SDS sodium dodecyl sulphate
SEQ. ID No. sequence identification number
siRNA small inhibitory ribonucleic acid
SirT2 NAD-dependent deacetylase sirtuin-2
SKBR3 human mammary carcinoma cell line
SKOV3 human ovarian carcinoma cell line
TUNEL terminal deoxynucleotidyl transferase dUTP nick end labeling
Tween polysorbate 20, non-ionic detergent
TX-100 Triton-X100
YO-PRO fluorescent, monomeric cyanine, nucleic acid stain

The invention claimed is:

1. A method for predicting the response to treatment of a neoplastic disease selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes;

or of an autoimmune disease selected from the group consisting of systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis, polymyositis, autoimmune hemolytic anemia, thrombocytopenic purpura, neutropenia, type I diabetes mellitus, thyroiditis (including Hashimoto's and Graves disease), Addison's disease, polyglandular syndrome, pemphigus, (vulgois, foliaceus, subaceous and vegetaus) bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (good syndrome), IgA nephropathy, pernicious anemia and autoimmune gastritis, inflammatory bowel diseases (including colitis ucerose and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory diseases with a possibility of autoimmune pathogensesis, such as pyoderma gangrensosum, lichen ruber, sarcoidosis, (including Lofgren and cutaneous subcutaneous type) granuloma anulare, allergic type I and type IV immunological reaction, asthma bronchiale, pollinosis, atopic, contact and airborne dermatitis, large vessel vasculitis, (Wegner's granulomatosis, Churg Strauss syndrome, microscopic polangiitis, HenochSchoenlein purpura, essential cryoglobulinemic vasculitis, cutaneous leukoklastic angritis), (grant cell and Takayase artheritis), medium sized vessel vasculitis (polyarteritis nodosa, Kawasaki disease), small vessel vasculitis (Wegner's granulomatosis, Churg Strauss syndrome, microscopic polangritis, HenochSchoenlein purpura essential cryoglobulinemic vasculitis, cutaneous leukoklastic angritis), hypersensitivity syndromes, toxic epidermal necrolysis (Stephens-Johnson syndrome, erythese multiform), diseases due to drug side effects, all forms of cutaneous, organ-specific and systemic effects due to type 1-vu (Coombs classification) immunologic forms of reaction and transplantation related pathologies, including acute and chronic graft verses host and host versus graft disease and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genitourinary system, ear, cartilage, primary and secondary lymphatic system including bone marrow, lymph node, thymus, gastrointestinal tract, including oro-pharynx, esophagus, stomach, small intestine, colon, and rectum, including parts of above mentioned organs down to single cell level and substructures, e.g. stem cells); in a patient subject by administration of a compound of general formula I

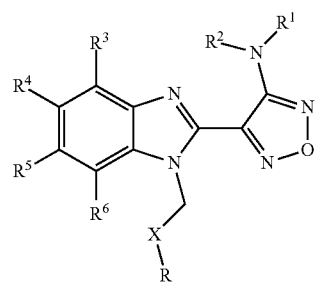

(I)

wherein
R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y,
wherein Y is oxygen or nitrogen substituted by hydroxy or lower alkoxy; or when R is optionally substituted phenyl or optionally substituted pyridinyl, X is additionally oxygen;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
or pharmaceutically acceptable derivatives thereof,
and wherein said prefix lower denotes a radical having up to 7 carbon atoms,
said method comprising the steps of:
a) measuring the level of the acetylated tubulin proteins in a sample obtained from a patient to obtain a value or values representing this level; and
b) comparing the value or values of the levels from step a) with a standard value or a set of standard values which comparison is predictive of responsiveness to compounds of formula I.

2. The method of claim 1, wherein said patient is an animal or human being and the level of acetylated tubulin proteins is measured ex vivo in the sample taken from said animal or human being.

3. The method according to claim 2, wherein the sample is derived from normal tissue, tumor tissue, circulating tumor cells, plasma or whole blood.

4. The method of claim 3, wherein a higher level of acetylated tubulin proteins in the sample relative to a standard value or a set of standard values predicts resistance to treating said disease with said compound of formula h or pharmaceutically acceptable derivatives thereof.

5. The method of claim 4, wherein the determination of a higher level of acetylated tubulin in said sample obtained from the animal or human being is carried out by comparing the measured acetylated tubulin protein level in said sample
 i) relative to a standard value or a set of standard values of levels of acetylated tubulin proteins from samples from other subjects having the same tumour histotype as said animal or human being; or
 ii) taken after treatment initiation and compared to a sample or samples taken from the same subject before treatment initiation; or
 iii) relative to a standard value or a set of standard values of levels of acetylated tubulin proteins from a sample or samples of levels of acetylated tubulin from normal tissue.

6. The method of claim 5, wherein the acetylated tubulin proteins are human alpha or beta tubulin, wherein a lysine residue in the protein sequence of the alpha or beta tubulin is acetylated.

7. The method of claim 6, wherein the protein sequence of acetylated tubulin is selected from the group consisting of SEQ ID No. 1, SEQ ID 2, SEQ ID 3, SEQ ID 4, SEQ ID 5, SEQ ID 6, and homologues, mutant forms, allelic variants, isoforms, splice variants and proteins with sequences having at least 75% identity to SEQ ID 1, SEQ ID 2, SEQ ID 3, SEQ ID 4, SEQ ID 5, or SEQ ID 6, with the proviso that a lysine residue in the protein sequence of the alpha or beta tubulin is acetylated.

8. The method of claim 5, wherein the acetylated tubulin proteins are human alpha tubulin proteins which comprise a lysine residue in position 40 of the protein sequence of an alpha tubulin protein, which is acetylated.

9. The method of claim 8, wherein the protein sequence of the acetylated tubulin proteins are selected from the group consisting of SEQ ID No. 1, SEQ ID 2, SEQ ID 3, and homologues, mutant forms, allelic variants, isoforms, splice variants and proteins with sequences having at least 75% identity to SEQ ID 1, SEQ ID 2 or SEQ ID 3 comprising a lysine residue in position 40 of the sequence and wherein said lysine residue in position 40 is acetylated.

10. The method of claim 1, wherein the compound is a compound of general formula I wherein R represents phenyl or pyridinyl wherein phenyl is optionally substituted by one or two substituents independently selected from lower alkyl, lower alkoxy, amino, acetylamino, halogen and nitro; and wherein pyridinyl is optionally substituted by amino or halogen;

X represents a group C=O;

R¹ represents hydrogen or cyano-lower alkyl;

R², R³, R⁴, R⁵ and R⁶ represent hydrogen;

or pharmaceutically acceptable derivatives thereof, and wherein said prefix lower denotes a radical having up to and including a maximum of 7.

11. The method according to claim 10, wherein said patient is an animal or human being and the level of acetylated tubulin proteins is measured ex vivo in a sample taken from the animal or human being's body.

12. The method according to claim 11, wherein the sample is derived from normal tissue, tumor tissue, circulating tumor cells, plasma or whole blood.

13. The method of claim 12, wherein a higher level of acetylated tubulin proteins in a sample obtained from said animal or human being relative to a standard value or a set of standard values predicts resistance to a therapy with compounds of formula I or pharmaceutically acceptable derivatives thereof.

14. The method of claim 13, wherein the determination of a higher level of acetylated tubulin in said sample obtained from the animal or human being is carried out by comparing the measured acetylated tubulin protein level in said sample i) relative to a standard value or a set of standard values of levels of acetylated tubulin proteins from samples from other subjects having the same tumour histotype as said animal or human being; or ii) taken after treatment initiation and compared to a sample or samples taken from the same subject before treatment initiation; or iii) relative to a standard value or a set of standard values of levels of acetylated tubulin proteins from a sample or samples of levels of acetylated tubulin from normal tissue.

15. The method of claim 10, wherein the acetylated tubulin proteins are used as biomarker to select subjects suffering or predisposed to suffering from a disease for treatment with a compound of general formula I or pharmaceutically acceptable derivatives thereof.

16. The method of claim 15, wherein the acetylated tubulin proteins are used as biomarker to select subjects suffering or predisposed to suffering from cancer for treatment with a compound of general formula I or pharmaceutically acceptable derivatives thereof.

17. The method of claim 10, wherein the acetylated tubulin proteins are used as biomarker to select subjects suffering or predisposed to suffering from a disease for treatment with a compound of general formula I or pharmaceutically acceptable derivatives thereof.

18. The method of claim 17, wherein the acetylated tubulin proteins are used as biomarker to select subjects suffering or predisposed to suffering from cancer for treatment with a compound of general formula I or pharmaceutically acceptable derivatives thereof.

19. The method of claim 10, wherein the compound is represented by the following formula

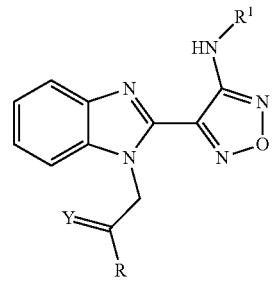

wherein R, Y and R1 are defined as follows:

| R | Y | R¹ |
|---|---|---|
| H₂N–⟨phenyl⟩– | O | CH₂CH₂CN |
| H₂N–⟨phenyl⟩– | O | H |
| H₂N–⟨pyridinyl⟩– | O | CH₂CH₂CN | or pharmaceutically acceptable derivatives thereof.

20. The method of claim 10, wherein the compound is

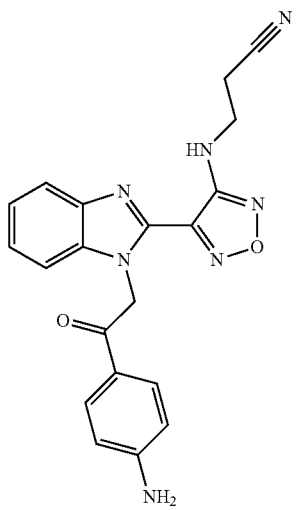

or pharmaceutically acceptable derivatives thereof.

21. The method of claim 10, wherein a pharmaceutically acceptable derivative is selected from the group consisting of a salt, solvate, pro-drug, salt of a pro-drug, polymorph and isomer of the compound of general formula I.

22. The method of claim 21, wherein the pharmaceutically acceptable pro-drug is an amide formed from an amino group present within the R group of the compound of formula I as defined in claim 10 and the carboxy group of glycine, alanine or lysine.

23. The method of claim 10 wherein a pharmaceutically acceptable derivative is selected from the group consisting of a salt, solvate, pro-drug, salt of a pro-drug, polymorph and isomer of the compound of general formula I as defined in claim 20.

24. The method of claim 23, wherein the pharmaceutically acceptable pro-drug is an amide formed from an amino group present within the R group of the compound of formula I as defined in claim 10 and the carboxy group of glycine, alanine or lysine.

25. The method of claim 10, wherein the compound is

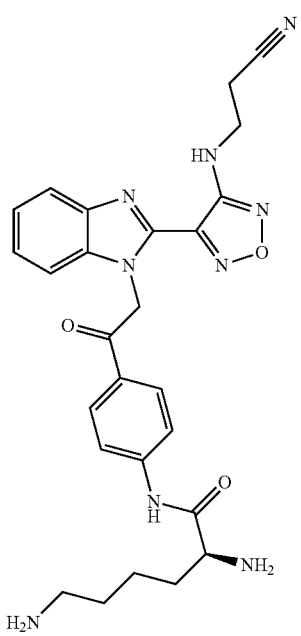 [SMILES: N#CCCNc1nonc1-c1nc2ccccc2n1CC(=O)c1ccc(NC(=O)[C@@H](N)CCCCN)cc1]

or a pharmaceutically acceptable salt thereof.

26. The method of claim 1, wherein the neoplastic disease is cancer and is selected from the group consisting of breast cancer, cervical cancer, ovarian cancer, T-cell leukemia and lung cancer.

27. The method of claim 26, wherein the cancer is selected from the group consisting of lung cancer, ovarian cancer and T-cell leukemia.

28. The method of claim 1, wherein the autoimmune disease is Sharp syndrome.

29. The method of claim 1, wherein the autoimmune disease is thyroiditis selected from the group consisting of Hashimoto's disease and Grave's disease.

30. The method of claim 1, wherein the autoimmune disease is pemphigus selected from the group consisting of pemphigus vulgaris, pemphigus foliaceus, pemphigus sebaceous and pemphigus vegetans.

31. The method of claim 1, wherein the autoimmune disease inflammatory bowel disease selected from the group consisting of colitis ulcerosa and morbus Crohn.

32. The method of claim 1, wherein the autoimmune disease is sarcoidosis selected from the group consisting of Lofgren sarcoidosis, cutaneous sarcoidosis and subcutaneous sarcoidosis.

33. The method of claim 1, wherein the autoimmune disease is large vessel vasculitis selected from the group consisting of giant cell vasculitits and Takayasu's arteritis.

34. The method of claim 1, wherein the autoimmune disease is medium sized vessel vasculitis selected from the group consisting of polyarteritis nodosa and Kawasaki disease.

35. The method of claim 1, wherein the autoimmune disease is small vessel vasculitis selected from the group consisting of Wegener's granulomatosis, Churg Strauss syndrome, microscopic polangiitis, HenochSchoenlein purpura, essential cryoglobulinemic vasculitis and cutaneous leukoklastic angiitis.

36. The method of claim 1, wherein the autoimmune disease is toxic epidermal necrolysis selected from the group consisting of Stevens-Johnson syndrome and erythema multiforme.

37. The method of claim 1, wherein the autoimmune disease is transplantation related pathologies selected from the group consisting of acute and chronic graft versus host and host versus graft disease.

38. The method of claim 1, wherein the disease is a neoplastic disease and the neoplastic disease is cancer.

39. The method of claim 38, wherein the disease is cancer and is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma, T-cell leukemia, and sarcomas.

40. The method of claim 1, wherein said disease is an autoimmune disease.

41. The method of claim 1, wherein the neoplastic disease is a cancer selected from the group consisting of breast, cervix, ovaries, colon, rectum, (including colon and rectum i.e. colorectal cancer) lung, (including small cell lung cancer, non-small cell lung cancer, large cell lung cancer and mesothelioma), endocrine systems, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis.

42. The method of claim 20, wherein the disease is breast cancer.

43. The method of claim 20, wherein the disease is ovarian cancer.

44. The method of claim 20, wherein the disease is colorectal cancer.

45. The method of claim 20, wherein the disease is lung cancer.

46. The method of claim 20, wherein the disease is liver cancer.

47. The method of claim 20, wherein the disease is gastric cancer.

48. The method of claim 20, wherein the disease is pancreatic cancer.

49. The method of claim 20, wherein the disease is hematological malignancy.

50. The method of claim 20, wherein the disease is kidney cancer.

51. The method of claim 20, wherein the disease is skin cancer.

52. The method of claim 20, wherein the disease is brain cancer.

53. The method of claim 20, wherein the disease is prostate cancer.

54. The method of claim 20, wherein the disease is head and neck cancer.

55. The method of claim 20, wherein the disease is a sarcomas.

56. The method of claim 20, wherein the disease is glioma.

57. The method of claim 25, wherein the disease is breast cancer.

58. The method of claim 25, wherein the disease is ovarian cancer.

59. The method of claim 25, wherein the disease is colorectal cancer.

60. The method of claim 25, wherein the disease is lung cancer.

61. The method of claim 25, wherein the disease is liver cancer.

62. The method of claim 25, wherein the disease is gastric cancer.

63. The method of claim 25, wherein the disease is pancreatic cancer.

64. The method of claim 25, wherein the disease is a hematological malignancy.

65. The method of claim 25, wherein the disease is kidney cancer.

66. The method of claim 25, wherein the disease is skin cancer.

67. The method of claim 25, wherein the disease is brain cancer.

68. The method of claim 25, wherein the disease is prostate cancer.

69. The method of claim 25, wherein the disease is head and neck cancer.

70. The method of claim 25, wherein the disease is a sarcomas.

71. The method of claim 25, wherein the disease is glioma.

72. The method according to claim 2, wherein the sample is derived from tumor tissue or circulating tumor cells.

73. The method according to claim 11, wherein the sample is derived from tumor tissue or circulating tumor cells.

74. A kit for predicting the response of a neoplastic disease selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell turnouts, immunoproliferative diseases, leukemias, miscellaneous myeloproliferative disorders, lymphoproliferative disorders and myelodysplastic syndromes;

or of an autoimmune disease selected from the group consisting of systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis, polymyositis, autoimmune hemolytic anemia, thrompocytopenic purpura, neutropenia, type I diabetes mellitus, thyroiditis (including Hashimoto's and Graves disease), Addison's disease, polyglandular syndrome, pemphigus, (vulgois, foliaceus, subaceous and vegetaus) bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (good syndrome), IgA nephropathy, pernicious anemia and autoimmune gastritis, inflammatory bowel diseases (including colitis ucerose and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory diseases with a possibility of autoimmune pathogensesis, such as pyoderma gangrensosum, lichen ruber, sarcoidosis, (including Lofgren and cutaneous subcutaneous type) granuloma anulare, allergic type I and type IV immunological reaction, asthma bronchiale, pollinosis, atopic, contact and airborne dermatitis, large vessel vasculitis, (Wegner's granulomatosis, Churg Strauss syndrome, microscopic polangiitis, HenochSchoenlein purpura, essential cryoglobulinemic vasculitis, cutaneous leukoklastic angritis), (grant cell and Takayase artheritis), medium sized vessel vasculitis (polyarteritis nodosa, Kawasaki disease), small vessel vasculitis (Wegner's granulomatosis, Churg Strauss syndrome, microscopic polangritis, HenochSchoenlein purpura essential cryoglobulinemic vasculitis, cutaneous leukoklastic angritis), hypersensitivity syndromes, toxic epidermal necrolysis (Stephens-Johnson syndrome, erythese multiform), diseases due to drug side effects, all forms of cutaneous, organ- specific and systemic effects due to type 1-vu (Coombs classification) immunologic forms of reaction and transplantation related pathologies, including acute and chronic graft versus host and host versus graft disease and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e.g. stem cells) to a compound of general formula 1 or a pharmaceutically acceptable derivative thereof, as defined in claim 1, comprising reagents necessary for measuring the level of acetylated tubulin proteins in a sample and a comparator module which comprises a standard value or set of standard values to which the level of acetylated tubulin proteins in the sample is compared.

75. The kit according to claim 74, wherein the reagents comprise:
   a) a capture reagent comprising a detector for acetylated tubulin proteins and
   b) a detection reagent.

76. The kit according to claim 75, wherein said capture reagent is an antibody.

77. The kit according to claim 76, wherein the kit comprises a compound of the following formula or a pharmaceutically acceptable salt thereof,

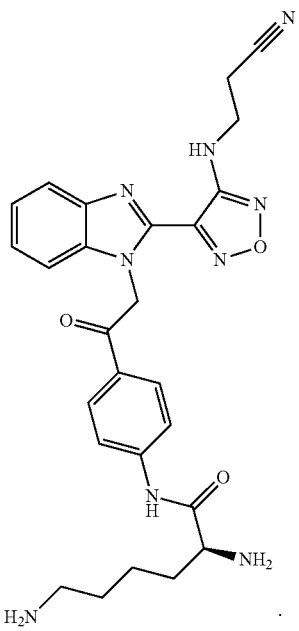 [SMILES: N#CCCNc1nonc1-c1nc2ccccc2n1CC(=O)c1ccc(NC(=O)[C@@H](N)CCCCN)cc1]

78. The kit of claim 77, wherein said salt is a hydrochloride salt.

* * * * *

```
                         SEQUENCE LISTING

<160> NUMBER OF SEQ ID NOS: 6

<210> SEQ ID NO 1
<211> LENGTH: 449
<212> TYPE: PRT
<213> ORGANISM: Homo sapiens

<400> SEQUENCE: 1

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
```

-continued

```
            145                 150                 155                 160
Tyr Gly Lys Lys Ser Lys Leu Glu Phe Ser Ile Tyr Pro Ala Pro Gln
                    165                 170                 175
Val Ser Thr Ala Val Val Glu Pro Tyr Asn Ser Ile Leu Thr Thr His
                180                 185                 190
Thr Thr Leu Glu His Ser Asp Cys Ala Phe Met Val Asp Asn Glu Ala
                195                 200                 205
Ile Tyr Asp Ile Cys Arg Arg Asn Leu Asp Ile Glu Arg Pro Thr Tyr
            210                 215                 220
Thr Asn Leu Asn Arg Leu Ile Ser Gln Ile Val Ser Ser Ile Thr Ala
225                 230                 235                 240
Ser Leu Arg Phe Asp Gly Ala Leu Asn Val Asp Leu Thr Glu Phe Gln
                    245                 250                 255
Thr Asn Leu Val Pro Tyr Pro Arg Ile His Phe Pro Leu Ala Thr Tyr
                260                 265                 270
Ala Pro Val Ile Ser Ala Glu Lys Ala Tyr His Glu Gln Leu Thr Val
                275                 280                 285
Ala Glu Ile Thr Asn Ala Cys Phe Glu Pro Ala Asn Gln Met Val Lys
290                 295                 300
Cys Asp Pro Arg His Gly Lys Tyr Met Ala Cys Cys Leu Leu Tyr Arg
305                 310                 315                 320
Gly Asp Val Val Pro Lys Asp Val Asn Ala Ala Ile Ala Thr Ile Lys
                    325                 330                 335
Thr Lys Arg Thr Ile Gln Phe Val Asp Trp Cys Pro Thr Gly Phe Lys
                340                 345                 350
Val Gly Ile Asn Tyr Gln Pro Pro Thr Val Val Pro Gly Gly Asp Leu
                355                 360                 365
Ala Lys Val Gln Arg Ala Val Cys Met Leu Ser Asn Thr Thr Ala Val
                370                 375                 380
Ala Glu Ala Trp Ala Arg Leu Asp His Lys Phe Asp Leu Met Tyr Ala
385                 390                 395                 400
Lys Arg Ala Phe Val His Trp Tyr Val Gly Glu Gly Met Glu Glu Gly
                    405                 410                 415
Glu Phe Ser Glu Ala Arg Glu Asp Met Ala Ala Leu Glu Lys Asp Tyr
                420                 425                 430
Glu Glu Val Gly Ala Asp Ser Ala Asp Gly Asp Glu Gly Glu Glu
                435                 440                 445
Tyr

<210> SEQ ID NO 2
<211> LENGTH: 450
<212> TYPE: PRT
<213> ORGANISM: Homo sapiens

<400> SEQUENCE: 2

Met Arg Glu Cys Ile Ser Ile His Val Gly Gln Ala Gly Val Gln Ile
1               5                   10                  15
Gly Asn Ala Cys Trp Glu Leu Tyr Cys Leu Glu His Gly Ile Gln Pro
                20                  25                  30
Asp Gly Gln Met Pro Ser Asp Lys Thr Ile Gly Gly Gly Asp Asp Ser
            35                  40                  45
Phe Asn Thr Phe Phe Ser Glu Thr Gly Ala Gly Lys His Val Pro Arg
        50                  55                  60
Ala Val Phe Val Asp Leu Glu Pro Thr Val Val Asp Glu Val Arg Thr
```

```
                65                  70                  75                  80
        Gly Thr Tyr Arg Gln Leu Phe His Pro Glu Gln Leu Ile Thr Gly Lys
                        85                  90                  95

Glu Asp Ala Ala Asn Asn Tyr Ala Arg Gly His Tyr Thr Ile Gly Lys
                100                 105                 110

Glu Ile Val Asp Leu Val Leu Asp Arg Ile Arg Lys Leu Ala Asp Leu
                115                 120                 125

Cys Thr Gly Leu Gln Gly Phe Leu Ile Phe His Ser Phe Gly Gly Gly
        130                 135                 140

Thr Gly Ser Gly Phe Ala Ser Leu Leu Met Glu Arg Leu Ser Val Asp
        145                 150                 155                 160

Tyr Gly Lys Lys Ser Lys Leu Glu Phe Ala Ile Tyr Pro Ala Pro Gln
                        165                 170                 175

Val Ser Thr Ala Val Val Glu Pro Tyr Asn Ser Ile Leu Thr Thr His
                180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
        210                 215                 220

Thr Asn Leu Asn Arg Leu Ile Gly Gln Ile Val Ser Ser Ile Thr Ala
        225                 230                 235                 240

Ser Leu Arg Phe Asp Gly Ala Leu Asn Val Asp Leu Thr Glu Phe Gln
                        245                 250                 255

Thr Asn Leu Val Pro Tyr Pro Arg Ile His Phe Pro Leu Ala Thr Tyr
                260                 265                 270

Ala Pro Val Ile Ser Ala Glu Lys Ala Tyr His Glu Gln Leu Ser Val
                275                 280                 285

Ala Glu Ile Thr Asn Ala Cys Phe Glu Pro Ala Asn Gln Met Val Lys
                290                 295                 300

Cys Asp Pro Arg His Gly Lys Tyr Met Ala Cys Cys Met Leu Tyr Arg
        305                 310                 315                 320

Gly Asp Val Val Pro Lys Asp Val Asn Ala Ala Ile Ala Thr Ile Lys
                        325                 330                 335

Thr Lys Arg Thr Ile Gln Phe Val Asp Trp Cys Pro Thr Gly Phe Lys
                340                 345                 350

Val Gly Ile Asn Tyr Gln Pro Pro Thr Val Val Pro Gly Gly Asp Leu
                355                 360                 365

Ala Lys Val Gln Arg Ala Val Cys Met Leu Ser Asn Thr Thr Ala Ile
                370                 375                 380

Ala Glu Ala Trp Ala Arg Leu Asp His Lys Phe Asp Leu Met Tyr Ala
        385                 390                 395                 400

Lys Arg Ala Phe Val His Trp Tyr Val Gly Glu Gly Met Glu Glu Gly
                        405                 410                 415

Glu Phe Ser Glu Ala Arg Glu Asp Leu Ala Ala Leu Glu Lys Asp Tyr
                420                 425                 430

Glu Glu Val Gly Val Asp Ser Val Glu Ala Glu Ala Glu Glu Gly Glu
                        435                 440                 445

Glu Tyr
            450

<210> SEQ ID NO 3
<211> LENGTH: 448
<212> TYPE: PRT
<213> ORGANISM: Homo sapiens
```

```
<400> SEQUENCE: 3

Met Arg Glu Cys Ile Ser Val His Val Gly Gln Ala Gly Val Gln Met
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Thr Thr Phe Phe Cys Glu Thr Gly Ala Gly Lys His Val Pro Arg
    50                  55                  60

Ala Val Phe Val Asp Leu Glu Pro Thr Val Ile Asp Glu Ile Arg Asn
65                  70                  75                  80

Gly Pro Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Pro Val Leu Asp Arg Ile Arg Lys Leu Ser Asp Gln
        115                 120                 125

Cys Thr Gly Leu Gln Gly Phe Leu Val Phe His Ser Phe Gly Gly Gly
130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Ala Ile Lys
                325                 330                 335

Thr Lys Arg Ser Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
```

```
            405                 410                 415
Glu Phe Ser Glu Ala Arg Glu Asp Met Ala Ala Leu Glu Lys Asp Tyr
            420                 425                 430
Glu Glu Val Gly Ile Asp Ser Tyr Glu Asp Glu Asp Glu Gly Glu Glu
            435                 440                 445

<210> SEQ ID NO 4
<211> LENGTH: 449
<212> TYPE: PRT
<213> ORGANISM: Homo sapiens

<400> SEQUENCE: 4

Met Arg Glu Cys Ile Ser Val His Val Gly Gln Ala Gly Val Gln Ile
1               5                   10                  15
Gly Asn Ala Cys Trp Glu Leu Phe Cys Leu Glu His Gly Ile Gln Ala
            20                  25                  30
Asp Gly Thr Phe Asp Ala Gln Ala Ser Lys Ile Asn Asp Asp Asp Ser
        35                  40                  45
Phe Thr Thr Phe Phe Ser Glu Thr Gly Asn Gly Lys His Val Pro Arg
    50                  55                  60
Ala Val Met Ile Asp Leu Glu Pro Thr Val Val Asp Glu Val Arg Ala
65                  70                  75                  80
Gly Thr Tyr Arg Gln Leu Phe His Pro Glu Gln Leu Ile Thr Gly Lys
                85                  90                  95
Glu Asp Ala Ala Asn Asn Tyr Ala Arg Gly His Tyr Thr Val Gly Lys
            100                 105                 110
Glu Ser Ile Asp Leu Val Leu Asp Arg Ile Arg Lys Leu Thr Asp Ala
        115                 120                 125
Cys Ser Gly Leu Gln Gly Phe Leu Ile Phe His Ser Phe Gly Gly Gly
    130                 135                 140
Thr Gly Ser Gly Phe Thr Ser Leu Leu Met Glu Arg Leu Ser Leu Asp
145                 150                 155                 160
Tyr Gly Lys Lys Ser Lys Leu Glu Phe Ala Ile Tyr Pro Ala Pro Gln
                165                 170                 175
Val Ser Thr Ala Val Val Glu Pro Tyr Asn Ser Ile Leu Thr Thr His
            180                 185                 190
Thr Thr Leu Glu His Ser Asp Cys Ala Phe Met Val Asp Asn Glu Ala
        195                 200                 205
Ile Tyr Asp Ile Cys Arg Arg Asn Leu Asp Ile Glu Arg Pro Thr Tyr
    210                 215                 220
Thr Asn Leu Asn Arg Leu Ile Ser Gln Ile Val Ser Ser Ile Thr Ala
225                 230                 235                 240
Ser Leu Arg Phe Asp Gly Ala Leu Asn Val Asp Leu Thr Glu Phe Gln
                245                 250                 255
Thr Asn Leu Val Pro Tyr Pro Arg Ile His Phe Pro Leu Val Thr Tyr
            260                 265                 270
Ala Pro Ile Ile Ser Ala Glu Lys Ala Tyr His Glu Gln Leu Ser Val
        275                 280                 285
Ala Glu Ile Thr Ser Ser Cys Phe Glu Pro Asn Ser Gln Met Val Lys
    290                 295                 300
Cys Asp Pro Arg His Gly Lys Tyr Met Ala Cys Cys Met Leu Tyr Arg
305                 310                 315                 320
Gly Asp Val Val Pro Lys Asp Val Asn Val Ala Ile Ala Ala Ile Lys
                325                 330                 335
```

Thr Lys Arg Thr Ile Gln Phe Val Asp Trp Cys Pro Thr Gly Phe Lys
                340                 345                 350

Val Gly Ile Asn Tyr Gln Pro Pro Thr Val Val Pro Gly Gly Asp Leu
            355                 360                 365

Ala Lys Val Gln Arg Ala Val Cys Met Leu Ser Asn Thr Thr Ala Ile
        370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Thr Asp Ser Phe Glu Glu Glu Asn Glu Gly Glu Glu
        435                 440                 445

Phe

<210> SEQ ID NO 5
<211> LENGTH: 444
<212> TYPE: PRT
<213> ORGANISM: Homo sapiens

<400> SEQUENCE: 5

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
                20                  25                  30

Thr Gly Thr Tyr His Gly Asp Ser Asp Leu Gln Leu Asp Arg Ile Ser
            35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

```
Met Val Pro Phe Pro Arg Leu His Phe Phe Met Pro Gly Phe Ala Pro
                260                 265                 270

Leu Thr Ser Arg Gly Ser Gln Gln Tyr Arg Ala Leu Thr Val Pro Glu
            275                 280                 285

Leu Thr Gln Gln Val Phe Asp Ala Lys Asn Met Met Ala Ala Cys Asp
        290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Glu Ala
                435                 440

<210> SEQ ID NO 6
<211> LENGTH: 450
<212> TYPE: PRT
<213> ORGANISM: Homo sapiens

<400> SEQUENCE: 6

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
                20                  25                  30

Ser Gly Asn Tyr Val Gly Asp Ser Asp Leu Gln Leu Glu Arg Ile Ser
            35                  40                  45

Val Tyr Tyr Asn Glu Ala Ser Ser His Lys Tyr Val Pro Arg Ala Ile
        50                  55                  60

Leu Val Asp Leu Glu Pro Gly Thr Met Asp Ser Val Arg Ser Gly Ala
65                  70                  75                  80

Phe Gly His Leu Phe Arg Pro Asp Asn Phe Ile Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Cys Glu Asn Cys Asp
        115                 120                 125

Cys Leu Gln Gly Phe Gln Leu Thr His Ser Leu Gly Gly Gly Thr Gly
130                 135                 140

Ser Gly Met Gly Thr Leu Leu Ile Ser Lys Val Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Ile His Gln Leu
            180                 185                 190
```

-continued

```
Val Glu Asn Thr Asp Glu Thr Tyr Cys Ile Asp Asn Glu Ala Leu Tyr
            195                 200                 205

Asp Ile Cys Phe Arg Thr Leu Lys Leu Ala Thr Pro Thr Tyr Gly Asp
            210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
            245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
            275                 280                 285

Leu Thr Gln Gln Met Phe Asp Ala Lys Asn Met Met Ala Ala Cys Asp
            290                 295                 300

Pro Arg His Gly Arg Tyr Leu Thr Val Ala Thr Val Phe Arg Gly Arg
305                 310                 315                 320

Met Ser Met Lys Glu Val Asp Glu Gln Met Leu Ala Ile Gln Ser Lys
            325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ser Ser Thr Phe Ile
            355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
            405                 410                 415

Asp Leu Val Ser Glu Tyr Gln Gln Tyr Gln Asp Ala Thr Ala Glu Glu
            420                 425                 430

Glu Gly Glu Met Tyr Glu Asp Asp Glu Glu Glu Ser Glu Ala Gln Gly
            435                 440                 445

Pro Lys
    450
```